(12) United States Patent
Assell et al.

(10) Patent No.: US 8,343,189 B2
(45) Date of Patent: Jan. 1, 2013

(54) METHOD AND APPARATUS FOR FACET JOINT STABILIZATION

(75) Inventors: Robert L. Assell, Wilmington, NC (US); Eugene A. Dickhudt, Lino Lakes, MN (US)

(73) Assignee: Zyga Technology, Inc., Minneapolis, MN (US)

( * ) Notice: Subject to any disclaimer, the term of this patent is extended or adjusted under 35 U.S.C. 154(b) by 764 days.

(21) Appl. No.: 12/238,196

(22) Filed: Sep. 25, 2008

(65) Prior Publication Data

US 2009/0138053 A1    May 28, 2009

Related U.S. Application Data

(60) Provisional application No. 60/995,141, filed on Sep. 25, 2007.

(51) Int. Cl.
*A61B 17/70* (2006.01)

(52) U.S. Cl. ........ 606/247; 606/246; 606/279; 606/301; 623/17.11

(58) Field of Classification Search .................. None
See application file for complete search history.

(56) References Cited

U.S. PATENT DOCUMENTS

| | | | |
|---|---|---|---|
| 2,677,369 A | 5/1954 | Knowles | |
| 3,426,364 A | 2/1969 | Lumb | |
| 3,879,767 A | 4/1975 | Stubstad | |
| 4,052,753 A | 10/1977 | Dedo | |
| 4,349,921 A | 9/1982 | Kuntz | |
| 4,502,161 A | 3/1985 | Wall | |
| 4,553,273 A | 11/1985 | Wu | |
| 4,554,914 A | 11/1985 | Kapp | |
| 4,599,086 A | 7/1986 | Doty | |
| 4,636,217 A | 1/1987 | Ogilvie | |
| 4,743,256 A | 5/1988 | Brantigan | |
| 4,834,757 A | 5/1989 | Brantigan | |
| 4,877,020 A * | 10/1989 | Vich | 606/86 R |
| 5,092,866 A | 3/1992 | Breard | |
| 5,147,404 A | 9/1992 | Downey | |
| 5,156,616 A | 10/1992 | Meadows | |
| 5,415,659 A | 5/1995 | Lee | |
| 5,415,661 A | 5/1995 | Holmes | |
| 5,496,318 A | 3/1996 | Howland et al. | |
| 5,507,823 A | 4/1996 | Walston | |
| 5,527,312 A | 6/1996 | Ray | |
| 5,571,191 A | 11/1996 | Fitz | |
| 5,609,634 A | 3/1997 | Voydeville | |
| 5,665,122 A * | 9/1997 | Kambin | 623/17.16 |

(Continued)

FOREIGN PATENT DOCUMENTS

DE         20112123         9/2001

(Continued)

*Primary Examiner* — David H Willse
*Assistant Examiner* — Javier Blanco
(74) *Attorney, Agent, or Firm* — Dicke, Billig & Czaja, PLLC

(57) ABSTRACT

A device for treating a facet joint of a patient, the facet joint including opposing, superior and inferior faces. The device includes a superior component and an inferior component each defining an anchoring surface configured to engage bone at a face of the facet joint and an articulating surface. The device is configured for percutaneous insertion into the facet joint, with the articulating surfaces abutting one another in a sliding interface. One or more instruments are included with the device as part of a percutaneous implantation kit, such as a dilator, a guide wire, and a sheath.

14 Claims, 14 Drawing Sheets

U.S. PATENT DOCUMENTS

| | | |
|---|---|---|
| 5,681,310 A | 10/1997 | Yuan |
| 5,683,464 A | 11/1997 | Wagner |
| 5,697,889 A | 12/1997 | Slotman |
| 5,968,098 A * | 10/1999 | Winslow .................... 623/17.11 |
| 6,019,792 A | 2/2000 | Cauthen |
| RE36,758 E | 6/2000 | Fitz |
| 6,102,948 A * | 8/2000 | Brosnahan, III ........... 623/17.16 |
| 6,126,688 A | 10/2000 | McDonnell |
| 6,132,464 A | 10/2000 | Martin |
| 6,132,468 A | 10/2000 | Mansmann |
| 6,156,067 A | 12/2000 | Bryan et al. |
| 6,179,874 B1 | 1/2001 | Cauthen |
| 6,287,313 B1 | 9/2001 | Sasso |
| 6,290,724 B1 * | 9/2001 | Marino ....................... 623/17.11 |
| 6,368,350 B1 | 4/2002 | Erickson et al. |
| 6,440,168 B1 | 8/2002 | Cauthen |
| 6,443,988 B2 | 9/2002 | Felt |
| 6,458,159 B1 | 10/2002 | Thalgott |
| 6,485,518 B1 | 11/2002 | Cornwall et al. |
| 6,540,747 B1 | 4/2003 | Marino |
| 6,544,265 B2 | 4/2003 | Lieberman |
| 6,562,046 B2 | 5/2003 | Sasso |
| 6,610,093 B1 | 8/2003 | Pisharodi |
| 6,652,585 B2 | 11/2003 | Lange |
| 6,652,587 B2 | 11/2003 | Felt |
| 6,679,915 B1 | 1/2004 | Cauthen |
| 6,733,531 B1 | 5/2004 | Trieu |
| 6,846,328 B2 | 1/2005 | Cauthen |
| 6,893,463 B2 | 5/2005 | Fell |
| 6,932,842 B1 | 8/2005 | Litschko |
| 6,966,930 B2 | 11/2005 | Arnin et al. |
| 6,974,478 B2 | 12/2005 | Reiley et al. |
| 6,986,771 B2 | 1/2006 | Paul |
| 6,989,011 B2 | 1/2006 | Paul |
| 7,001,431 B2 | 2/2006 | Bao |
| 7,041,136 B2 | 5/2006 | Goble et al. |
| 7,087,084 B2 | 8/2006 | Reiley |
| 7,101,398 B2 | 9/2006 | Dooris |
| 7,115,131 B2 | 10/2006 | Engh |
| 7,115,132 B2 | 10/2006 | Errico |
| 7,115,142 B2 | 10/2006 | Muhanna |
| 7,147,665 B1 | 12/2006 | Bryan et al. |
| 7,270,681 B2 | 9/2007 | Cauthen |
| 7,291,169 B2 | 11/2007 | Hodorek |
| 7,371,238 B2 | 5/2008 | Soboleski |
| 7,377,942 B2 | 5/2008 | Berry |
| 7,468,075 B2 | 12/2008 | Lang |
| 7,476,252 B2 * | 1/2009 | Foley ......................... 623/17.16 |
| 7,591,851 B2 | 9/2009 | Winslow |
| 7,618,451 B2 | 11/2009 | Berez |
| 7,708,761 B2 | 5/2010 | Petersen |
| 7,744,612 B2 | 6/2010 | Blain |
| 7,776,090 B2 | 8/2010 | Winslow |
| 7,846,183 B2 | 12/2010 | Blain |
| 7,922,766 B2 | 4/2011 | Grob |
| 7,927,374 B2 | 4/2011 | Duggal |
| 7,935,134 B2 * | 5/2011 | Reglos et al. .................. 606/257 |
| 7,938,836 B2 * | 5/2011 | Ainsworth et al. ............. 606/99 |
| 7,938,857 B2 * | 5/2011 | Garcia-Bengochea et al. ....... 623/17.11 |
| 7,955,355 B2 * | 6/2011 | Chin ............................. 606/246 |
| 7,998,172 B2 | 8/2011 | Blain |
| 8,100,955 B2 | 1/2012 | Blain |
| 2001/0051807 A1 | 12/2001 | Grafton |
| 2002/0026244 A1 | 2/2002 | Trieu |
| 2002/0055737 A1 | 5/2002 | Lieberman |
| 2002/0120270 A1 | 8/2002 | Trieu |
| 2002/0143329 A1 | 10/2002 | Serhan |
| 2002/0151895 A1 | 10/2002 | Soboleski |
| 2003/0028250 A1 | 2/2003 | Reiley |
| 2003/0176871 A1 | 9/2003 | Pavlov et al. |
| 2003/0208202 A1 | 11/2003 | Falahee |
| 2003/0220643 A1 | 11/2003 | Ferree |
| 2004/0010312 A1 | 1/2004 | Enayati |
| 2004/0049280 A1 * | 3/2004 | Cauthen .................... 623/17.14 |
| 2004/0087954 A1 | 5/2004 | Allen et al. |
| 2004/0143332 A1 | 7/2004 | Krueger |
| 2004/0153159 A1 * | 8/2004 | Cauthen .................... 623/17.14 |
| 2004/0225360 A1 | 11/2004 | Malone |
| 2004/0236328 A1 | 11/2004 | Paul |
| 2004/0260287 A1 | 12/2004 | Ferree |
| 2005/0021029 A1 | 1/2005 | Trieu |
| 2005/0027361 A1 | 2/2005 | Reiley |
| 2005/0049705 A1 | 3/2005 | Hale et al. |
| 2005/0076974 A1 | 4/2005 | Blain |
| 2005/0080486 A1 | 4/2005 | Fallin et al. |
| 2005/0085912 A1 | 4/2005 | Arnin et al. |
| 2005/0119748 A1 | 6/2005 | Reiley et al. |
| 2005/0125062 A1 | 6/2005 | Biedermann |
| 2005/0143818 A1 | 6/2005 | Yuan et al. |
| 2005/0143825 A1 | 6/2005 | Enayati |
| 2005/0159746 A1 * | 7/2005 | Grob et al. ........................ 606/61 |
| 2005/0177240 A1 * | 8/2005 | Blain ......................... 623/17.15 |
| 2005/0197700 A1 | 9/2005 | Boehm |
| 2005/0197706 A1 | 9/2005 | Hovorka |
| 2005/0251256 A1 | 11/2005 | Reiley |
| 2005/0273100 A1 | 12/2005 | Taylor |
| 2006/0009847 A1 | 1/2006 | Reiley |
| 2006/0036243 A1 | 2/2006 | Sasso |
| 2006/0036323 A1 | 2/2006 | Carl et al. |
| 2006/0041311 A1 | 2/2006 | McLeer |
| 2006/0064099 A1 | 3/2006 | Pavlov et al. |
| 2006/0084977 A1 | 4/2006 | Lieberman |
| 2006/0085068 A1 | 4/2006 | Barry |
| 2006/0111779 A1 | 5/2006 | Peterson |
| 2006/0111780 A1 | 5/2006 | Peterson |
| 2006/0111781 A1 | 5/2006 | Peterson |
| 2006/0111782 A1 | 5/2006 | Petersen |
| 2006/0116768 A1 | 6/2006 | Krueger |
| 2006/0122701 A1 | 6/2006 | Kiester |
| 2006/0149374 A1 | 7/2006 | Winslow |
| 2006/0155297 A1 * | 7/2006 | Ainsworth et al. ............. 606/99 |
| 2006/0190081 A1 | 8/2006 | Kraus et al. |
| 2006/0235391 A1 | 10/2006 | Sutterlin |
| 2006/0235403 A1 | 10/2006 | Blain |
| 2006/0235409 A1 | 10/2006 | Blain |
| 2006/0235412 A1 | 10/2006 | Blain |
| 2006/0235518 A1 | 10/2006 | Blain |
| 2006/0235533 A1 | 10/2006 | Blain |
| 2006/0241758 A1 | 10/2006 | Peterman et al. |
| 2006/0247632 A1 | 11/2006 | Winslow |
| 2006/0247633 A1 | 11/2006 | Winslow et al. |
| 2006/0276790 A1 | 12/2006 | Dawson et al. |
| 2006/0276907 A1 * | 12/2006 | Boyer et al. ................. 623/23.51 |
| 2007/0032790 A1 | 2/2007 | Aschmann et al. |
| 2007/0055236 A1 | 3/2007 | Hudgins |
| 2007/0055252 A1 | 3/2007 | Blain |
| 2007/0055373 A1 | 3/2007 | Hudgins et al. |
| 2007/0067032 A1 | 3/2007 | Felt et al. |
| 2007/0083265 A1 | 4/2007 | Malone |
| 2007/0083266 A1 | 4/2007 | Lang |
| 2007/0088358 A1 | 4/2007 | Yuan et al. |
| 2007/0100450 A1 | 5/2007 | Hodorek |
| 2007/0118218 A1 | 5/2007 | Hooper |
| 2007/0123863 A1 | 5/2007 | Winslow et al. |
| 2007/0135814 A1 | 6/2007 | Farris |
| 2007/0135919 A1 | 6/2007 | Aebi et al. |
| 2007/0149976 A1 | 6/2007 | Hale et al. |
| 2007/0161991 A1 * | 7/2007 | Altarac et al. .................. 606/61 |
| 2007/0167946 A1 | 7/2007 | Triplett |
| 2007/0179608 A1 | 8/2007 | Ek et al. |
| 2007/0225813 A1 | 9/2007 | Haines |
| 2007/0276370 A1 * | 11/2007 | Altarac et al. .................. 606/61 |
| 2007/0276498 A1 | 11/2007 | Aebi et al. |
| 2007/0276499 A1 * | 11/2007 | Paul et al. ................... 623/17.16 |
| 2008/0009875 A1 | 1/2008 | Sankaran |
| 2008/0027543 A1 | 1/2008 | Eisermann |
| 2008/0027547 A1 | 1/2008 | Yu |
| 2008/0033440 A1 * | 2/2008 | Moskowitz et al. ............. 606/72 |
| 2008/0045954 A1 | 2/2008 | Reiley et al. |
| 2008/0051901 A1 | 2/2008 | De Villiers |
| 2008/0091199 A1 | 4/2008 | Cragg |
| 2008/0097613 A1 | 4/2008 | Reiley et al. |
| 2008/0119933 A1 | 5/2008 | Aebi et al. |
| 2008/0125814 A1 | 5/2008 | Yuan et al. |
| 2008/0132951 A1 | 6/2008 | Reiley et al. |

| | | |
|---|---|---|
| 2008/0140121 A1 | 6/2008 | McLeer |
| 2008/0143818 A1 | 6/2008 | Ferren |
| 2008/0154305 A1 | 6/2008 | Foley et al. |
| 2008/0208249 A1 | 8/2008 | Blain |
| 2008/0262555 A1* | 10/2008 | Assell et al. .......... 606/301 |
| 2009/0062920 A1 | 3/2009 | Tauber |
| 2009/0088846 A1 | 4/2009 | Myung |
| 2009/0138053 A1* | 5/2009 | Assell et al. .......... 606/301 |
| 2009/0177205 A1* | 7/2009 | McCormack et al. ......... 606/90 |
| 2009/0234458 A1 | 9/2009 | De Villiers |
| 2009/0264928 A1 | 10/2009 | Blain |
| 2010/0131008 A1 | 5/2010 | Overes |
| 2010/0228288 A1 | 9/2010 | Blain |
| 2010/0249937 A1 | 9/2010 | Blain |
| 2010/0274286 A1 | 10/2010 | Blain |
| 2010/0286778 A1 | 11/2010 | Eisermann |
| 2010/0292797 A1 | 11/2010 | Lindner |
| 2011/0022089 A1* | 1/2011 | Assell et al. .......... 606/247 |
| 2011/0040301 A1 | 2/2011 | Blain |
| 2011/0060366 A1 | 3/2011 | Heim |
| 2011/0082503 A1 | 4/2011 | Blain |
| 2011/0313456 A1 | 12/2011 | Blain |

FOREIGN PATENT DOCUMENTS

| | | |
|---|---|---|
| DE | 202007015081 | 1/2008 |
| DE | 202009006906 | 7/2009 |
| EP | 381588 | 8/1990 |
| FR | 2681525 | 3/1993 |
| FR | 2717675 | 9/1995 |
| WO | 9310725 | 6/1993 |
| WO | 9405235 | 3/1994 |
| WO | 0234147 | 2/2002 |
| WO | 0245765 | 6/2002 |
| WO | 02065954 | 8/2002 |
| WO | 2005072661 | 8/2005 |
| WO | 2005076974 | 8/2005 |
| WO | 2006020464 | 2/2006 |
| WO | 2006065774 | 6/2006 |
| WO | 2006096803 | 9/2006 |
| WO | 2007/019215 A2 | 2/2007 |
| WO | 2009143496 | 11/2009 |
| WO | 2011011621 | 1/2011 |

* cited by examiner

METHOD AND APPARATUS FOR FACET JOINT STABILIZATION

CROSS-REFERENCE TO RELATED APPLICATIONS

This application claims priority under 35 U.S.C. §119(e)(1) to U.S. Provisional Patent Application Ser. No. 60/995,141, filed Sep. 25, 2007, entitled "Method and Apparatus for Facet Joint Stabilization"; and the entire teachings of which are incorporated herein by reference.

FIELD

The present disclosure relates generally to spinal devices introduced percutaneously through tissue to an access point on the spine in a minimally-invasive, low trauma manner, to provide therapy to the spine. The devices supplement physiologic structures of the spine and are generally introduced via a posterior approach through instrumentation systems and procedures that deploy implantable components and assemblies which are anchored in bone and distract, decompress, and resurface human spinal joints thereby stabilizing the joints to relieve lower back pain, restore physiological function of the spine, and prevent progression or transition of degenerative disease. More specifically, the spinal devices may be used to augment and stabilize one or more facet joints at various levels on the posterior spinal column. Additionally, the devices may similarly be configured and adapted to provide therapeutic advantages for use in other spinal joints, such as the sacroiliac joints, and in other articular joints.

BACKGROUND

Within the next 10 years, more than 70 million people are going to join the ranks of seniors. In an aging population, the articular cartilage that allows bones to smoothly move over each other wears down with time and unlike many tissues in the body, articular cartilage cannot heal itself. At this time, options that help to relieve severe degenerative joint pain, or osteoarthritis, include joint replacement or fusion. As examples, approximately 200,000 total knee joint and over 300,000 hip joint replacement operations are performed annually, and typically these artificial joints last about 10 to 15 years. Chronic lower back pain also affects both workforce productivity and health care expense, and there are currently over 500,000 surgical procedures performed annually in the United States in an attempt to alleviate lower back pain that persists following failure of more conservative therapy (e.g., bed rest, pain and muscle relaxant medication, physical therapy or steroid injection). The source of this pain may originate from dysfunction among a plurality of anatomical structures (as will be shown and described below) that are comprised in the spine, including facet joints.

Facet joints can become arthritic due to degeneration with aging, trauma, or disease (e.g., pathologies that include inflammatory, metabolic, or synovial, disorders). In addition, fractures, torn ligaments, and disc problems (e.g., dehydration or herniation) can all cause abnormal movement and alignment, putting extra stress on the surfaces of the facet joints.

The physiological response to this extra pressure is the development of osteophytes, i.e., bone spurs. As the spurs form around the edges of the facet joints, the joints become enlarged, a condition called hypertrophy, and eventually the joint surfaces become arthritic. When the articular cartilage degenerates, or wears away, the bone underneath is uncovered and rubs against bone. The joint becomes inflamed, swollen, and painful.

Facet joint arthritis is a significant source of neck and back pain, and attributable to about 15 percent of persistent lower back pain. Upon failure of conservative treatment for facet joint pain, such as intra-articular steroid/local anesthetic injections administered under fluoroscopic guidance, some patients with chronic pain may eventually require surgical intervention for facet joint arthritis including, for example, facet rhizotomy; facetectomy to remove the facet joint to reduce pressure on the exiting nerve root; total joint replacement, or facet arthrodesis (i.e., fixation leading to fusion, where the two articulating surfaces of the joint grow solidly together and form a single, solid piece of bone). However, as will be noted in more detail below, while these surgical procedures may alleviate back pain, many joint replacements and all fusions do not restore the normal physiological function and motion attributable to healthy anatomical form. Rather, they often significantly alter spinal biomechanics which can cause or exacerbate co-existing spinal instabilities and degeneration at other spinal levels or in other joints associated with spinal motion.

To understand spinal biomechanics, and the impacts of dysfunction and therapy, it is perhaps useful to first consider the spinal anatomy. The vertebrae of the spinal cord are conventionally subdivided into several sections. Moving from the head (cephalad) to the tailbone (caudal), the sections are cervical, thoracic, lumbar, sacral, and coccygeal. Regardless of location, each vertebra forms two pedicles and two laminae that combine to define a spinal foramen in which the spinal cord is protected. Extending from the pedicles are two transverse processes. Extending from the midline of the vertebra where the two laminae meet is a spinous process. These three processes serve as a connection point for ligaments and muscles. Adjacent vertebrae are separated by an intervertebral disc, and surfaces of the adjacent vertebrae form portions of two fact joints by and between the two vertebrae (it being understood that relative to a spinal segment consisting of an intermediate vertebra, an adjacent cephalad vertebra, and an adjacent caudal vertebra, the intermediate vertebra forms portions of four facet joints, two facet joints with the cephalad vertebra and two facet joints with the cephalad vertebra).

As illustrated in FIG. 1, a facet joint 20 is composed of a superior facet 22 and an inferior facet 24. The superior facet 22 is formed by the vertebral level below the intervertebral disc (a superior articular facet faces upward from the junction of the lateral mass and the pedicle) and the inferior facet 24 is formed by the vertebral level above the intervertebral disc (an inferior articular facet, which faces downward). On the superior articular facet 22 is a superior articulating surface, and on the inferior articular facet 24 is an inferior articulating surface. Facet joints are oriented obliquely to the sagittal plane, and the joint space itself is curved from front to back. The more posteriorly located inferior facet 24 is convex, whereas the more anteriorly located superior facet 22 is concave. There are two facet joints between each pair of vertebrae, one on each side, from the top and bottom of each vertebra. The joints combine with the disc space to create a three-joint complex at each vertebral level, and each joint extends and overlaps neighboring vertebral facet joints, linking each other and hence the vertebrae together. The facet joints are synovial joints; each joint including two opposing bony surfaces with cartilage 26 between them and a capsule 28 around the joint. More specifically, synovial fluid 30 is contained inside the joint by the joint capsule 28, a watertight sac of soft tissue and ligaments that fully surrounds and encloses the joint, which keeps the joint surfaces lubricated. The ends of the bones 22, 24 that make up the synovial facet joint 20 are normally covered with articular, hyaline cartilage that allows the bones to glide against one another providing the flexibility that allows the movement of vertebral bodies relative to one another.

The assembly of two vertebral bodies, the interposed spinal disc and the attached ligaments, muscles and facet joints (the inferior articular processes that articulate with the superior articular processes of the next succeeding vertebra in the caudal direction) is referred to as a "spinal motion segment." Each motion segment contributes to the overall flexibility of the spine and contributes to the overall ability of the spine to provide support for the movement of the trunk and head, and in particular, the facet joints enable torsional (twisting) stability. When the facets of one or more vertebral bodies degenerate, or otherwise become damaged such that the vertebrae no longer articulate or properly align with each other, there is a resulting loss of mobility, and pain or discomfort. The functional role of facet joints in a spinal motion segment is thus relevant to an understanding of the operative and functional advantages of the facet joint methods and devices disclosed herein, which achieve dynamic stabilization and mobility preservation without constraining motion in any plane.

In the context of the present disclosure, "dynamic" refers to non-static devices with an inherent ability to allow mobility by enabling or facilitating force or load bearing that assist or substitute for physiological structures that are otherwise compromised, weakened or absent. The spinal motion preservation assemblies of the present disclosure provide dynamic stabilization across a progression-of-treatment interventions for treating symptomatic joint pain.

As indicated above, facet joints are located on the posterior column of the spine. In the context of this discussion: anterior refers to in front of the spinal column, and posterior refers to behind the column; cephalad means towards a patient's head (sometimes "superior"); caudal (sometimes "inferior") refers to the direction or location that is closer to a patient's feet. As the present application contemplates accessing various vertebral elements and joints through a preferred approach that comes in from a percutaneous posterior approach, proximal and distal are defined in context of this channel of approach. Consequently, proximal is closer to the beginning of the channel and thus closer to the clinician, distal is farther from the beginning of the channel and thus more distant from the clinician. When referencing access and delivery tools, distal would be the end intended for insertion into the access channel, and proximal refers to the opposing end, generally the end closer to the handle for the delivery tool. When referencing implants, generally distal would be the leading end first inserted into the joint, and proximal refers to the trailing end, generally the end in engagement with the deployment tool.

There is a cause-and-effect relationship among intervertebral disc integrity, facet loads and spinal degeneration. Specifically, the progressive loss of disc height with disc degeneration often also alters the facet joint's mechanical ability as the facet joints may degenerate or dislocate, and the physiologic ligaments lose elasticity and their load carrying ability. More specifically, with disc-space narrowing, as frequently occurs with degenerative disc disease, there is increased load in the facet joints, especially in extension, and concomitant degeneration of the facet joints and capsules. Since the facet joint capsules are primarily loaded in flexion and in rotation, and the facet joints are the primary resistors against rotational or torsional forces (e.g., normally the facets control approximately 30% of axial rotation), facet joint degeneration significantly alters spinal mobility.

The need to provide minimally invasive therapies that provide pain relief while restoring and preserving the biomechanical function of the physiologic facet joints is paramount to overall spinal mobility, and to date, therapies have not adequately satisfied all of these issues, as noted below.

One therapy, facet rhizotomy, involves techniques that sever small nerves that go to the facet joint. The intent of the procedure is to stop the transmission of pain impulses along this nerve. The nerve is identified using a diagnostic injection. Then the surgeon inserts a large, hollow needle through the tissues in the low back. A radiofrequency probe is inserted through the needle, and a fluoroscope is used to guide the probe toward the nerve. The probe is slowly heated until the nerve is severed. Another technique using pulsed radiofrequency does not actually burn the nerve, rather, it is believed to stun the nerve. Yet another technique involves de-enervation by probe tip freezing, and still another procedure involves carefully controlled injection of botox toxin to treat muscle spasm, a protective reflex that may occur when the facets are inflamed which causes the nearby muscles that parallel the spine to go into spasm. While these procedures may provide pain relief, they do not address ongoing joint degeneration, e.g., wear on articulating surfaces, which leads to kinematic and biomechanical dysfunction that may in turn lead to transition syndrome (i.e., progression of degeneration and pain in other joints) at other levels.

While certain clinicians have advocated prosthetic total joint replacement of damaged facet joints, in practice it is difficult to implement a prosthetic facet joint for a variety of reasons including the variability in facet joint geometry from facet joint to facet joint and the high level of interaction between the facet joint and the other components in the spinal column. Moreover, joint replacement is an invasive and time-consuming procedure, requiring pre-preparation of joint surfaces and removal of bone, and thus there are associated risks, including blood loss and morbidity, increased anesthesia time, and increased convalescence time.

Another therapeutic treatment of the facet joint is to affix the superior articular process to the inferior articular process using a facet screw. Although this fixation therapy may alleviate symptoms associated with a degenerated facet joint, it also sacrifices some of the ability of the motion segment to move and thus sacrifices some of the ability of the spinal column to move in a natural manner. Central and lateral spinal stenosis (joint narrowing), degenerative spondylolisthesis, and degenerative scoliosis may all result from the abnormal mechanical relationship between the anterior and posterior column structures, and induce debilitating pain.

Still another therapeutic treatment of the facet joint, known in the prior art, involves an artificial facet joint where the inferior facet, the mating superior facet, or both, are covered with a cap, i.e., over (substantively all of) the facet. While potentially viable, the capping of the facet has several potential disadvantages. If the facet joint is osteoarthritic, a cap will not remove the source of the pain. Moreover, at least with use of caps over osteoarthritic femoral heads, the capping of articular bone ends has sometimes experienced clinical failure by mechanical loosening. This clinical failure is believed to result from the disruption of the periosteum and ligamenturn teres femoris, both serving a nutrition delivery role to the femoral head, thereby leading to avascular necrosis of the bony support structure for the cap. It is likely that corresponding problems could develop from capping the facet. Another potential disadvantage of facet capping is that in order to accommodate the wide variability in anatomical morphology of the facets, not only between individuals but also between levels within the spinal column, a very wide range of cap sizes and shapes is required.

Thus, there is an unmet need for additional therapies applicable to facet joints to stabilize and augment the facet joint to alleviate problems without initial resort to the more radical therapies of replacing the facet joint with a prosthetic joint or fixation of the facet joint and the inherent loss of natural movement of that motion segment.

SUMMARY

In accordance with some aspects of the present disclosure, anchored articulating implant assemblies are configured to provide therapy (arthroplasty) to, and dynamic stabilization of, degenerative spinal joints (e.g., facet joints; sacroiliac joints). Facet joints are bearing surfaces that exhibit extremely low wear properties. The methods and apparatus taught in the present disclosure fulfill a need for a system of facet joint augmentation and resurfacing of (residual) articular hyaline cartilage and/or bone that is minimally-invasive yet able to satisfy the biomechanical and kinematic requirements of the natural facet joint, via implants configured to allow motion between adjacent bones of the facet joint, that preserve motion by precluding further degeneration of articulating surfaces in the joint, and that distract and decompress the joint (as will be described below), to provide pain relief.

The methods and apparatus of the present disclosure, in addition to overcoming one or more of the problems and disadvantages associated with current designs in various treatments for adult spine diseases, can provide therapy as a primary or an adjunct procedure or in a progression of treatment strategy, i.e., are revisable in that they may be followed by a more traditional treatment option at a later date should the need for treatment evolve to require the more invasive or radical treatment. The use of the novel motion preservation treatment options disclosed in the present application provide dynamic stabilization while avoiding the problems of spine stiffness or increased loads on other joints or motion segments on other levels. The methods and apparatus of the present disclosure pertain to spinal prostheses designed to repair, such as by resurfacing, articulating joints at virtually all spinal levels, and additionally, may be configured to provide therapy to other articulating joints elsewhere in the body.

Exemplary methods, instrumentation systems, and implant assemblies of the present disclosure are directed to surgical treatment of facet joints using spinal motion preservation devices that dilate and augment the facet joints via inserting and affixing into the facet joint a prosthetic "liner" that serves to repair the articulating surfaces of the joint. More specifically, in one aspect of the disclosure, the implant assembly "resurfaces" the native joint surface with a metal-on-bone liner that also serves as a spacer. In one example, the prosthetic liner is generally configured as an assembly including a superior facet implant component and an inferior facet implant component, wherein each implant component (hereinafter sometimes for convenience, also individually "component," or in context, collectively "components," for the superior facet implant and the inferior facet implant) mates with the other (e.g., as a longitudinally cross-sectioned half of a whole), and is constructed as an elongate, hemicylindrical rod including a leading end, and a trailing end, the rod assembly fabricated from, e.g., cobalt-chrome alloy or such other high tensile strength, wear-resistant, biocompatible metal or metal alloy appropriate for joint resurfacing. A first, curvilinear surface of each implant component half is configured with anchoring feature(s) to engage with and affix the device into the facet joint bone. Opposing the first cylindrical anchoring surface of each component rod is a second surface, that may be curvilinear or substantially axial (linear), that serves as an articulating surface. When deployed into the facet joint, the articulating surfaces (which can be substantially flat) of each component of the implant assembly abut, one against the other, so that these surfaces are in axial sliding engagement along substantively the length of the articulating surfaces, and are precluded from rotational misalignment via the components' respective anchoring in the bone. The trailing end of the superior facet component and the trailing end of the inferior facet component are each configured as (substantially) "half" of a female engagement fixture (such as a slot, or hex) to a corresponding male engagement fixture included in an introducer-driver sub-assembly configured to insert a spinal motion preservation implant assembly into a facet joint.

In the context of the present disclosure, the term "spacer" refers to the physical dimensionality and presence of an implant assembly, e.g., wherein insertion of the anchored implant assembly between the superior and inferior articulating surfaces of a facet joint both increases and maintains a given distance between the surfaces.

Thus, in addition to providing prosthetic articulating surfaces, yet another advantage of the present disclosure is that the insertion of the implant assemblies into the joint dilates the facet joint (e.g., the implant assemblies serve as spacers), increasing the distance between the inferior articular process and the superior articular process. This is known as distraction. Increasing the distance between the inferior articular process of one vertebra and the superior articular process of an adjacent more caudal vertebra will alter the relative positions of the two vertebrae and may alter the loading on the intervertebral disc that lies between the vertebral bodies of that motion segment. Increasing this distance may also separate two painful facet joint surfaces, and may also enlarge a stenotic spinal canal and stenotic neuralforamina to relieve compressed nerves.

In yet another aspect of the present disclosure, examples are directed to instrumentation systems for minimally-invasive, percutaneous posterior access and preparation for surgical intervention and methods for use by which the natural facet joints of the spine may be augmented by an anchored articulating implant assembly, the method optionally consisting of: identifying the location of the facet joint to be augmented via an image-guided system, including radiologic, or fluoroscopic methods, or the like; identifying a point of entry on the patient's skin and establishing a trajectory to the subcutaneous facet joint to be resurfaced; percutaneously inserting a guide pin (or alternatively, a dilator-guide pin assembly) through the point of entry to a target site, through the capsule and into the articular space of the facet joint to be repaired, and verifying the location of the leading end of the guide pin using the image-guided system; inserting a dilator (or alternatively, a plurality of dilators of sequentially increasing diameter) over the guide pin and docking the dilator into the facet; passing a dilator sheath or cannula over the guide pin and inserting it concentrically over the dilator, so that upon subsequent removal of the dilator, the cannula provides a working channel into the surgical field of the facet joint to be repaired; inserting a drill or other bore method to create a pilot hole through the working channel; inserting a tap over the guide wire and through the working channel to pre-thread the pilot hole and then removing the guide wire; inserting an introducer driver-introducer tube assembly that is pre-loaded with the articulating implant assembly; inserting, aligning, and anchoring the implant assembly to provide prosthetic articulating surfaces for, and dilation of, the facet joint thereby alleviating pain, restoring and preserving motion, and stabilizing the joint to preclude progressive degeneration.

Additional examples are directed to medical kits for spinal joint therapies, for example, such as for facet joints, via minimally-invasive, percutaneous interventions. The kits may include some or all of the components and instrumentation system necessary for accessing and preparing the target surgical site and for deploying the implant assemblies and therapies described in the disclosure. The kits may also include prosthetic implants in a variety of sizes and configurations to address the variations in facet joints from one portion of a spine to another, from one patient to another, and to address irregularities that may be present from degeneration of the facet joint.

One advantage of the spinal joint therapies of the present disclosure is that resurfacing of facets represents a bone conserving alternative to conventional total joint replacement or arthroplasty. It is an object of the disclosure to achieve resurfacing of the facet joint articular surfaces with minimal disruption of the blood supply to the adjacent bone. Implantation of the prostheses in the present disclosure disrupts virtually none of the periosteal layer on the bones including the facet joint. That is, unlike prior art procedures that "cap" facets joints, where the outer surface of the bones including the facet joints is removed and reshaped in order to allow placement of the apparatus, a process which will rob the bone of its source of blood and therefore nutrition, the joint resurfacing methods and apparatus of the present disclosure maintain the health of the bone while providing a method to firmly affix the implant and effectively augment the articular surfaces.

It is an object of the implant assemblies of the present disclosure to provide therapy for patients in whom additional surgery may be required within their lifetime based upon their age, activity level and other factors. More specifically, the methods and apparatus for resurfacing spinal joints disclosed in the present disclosure is achieved without invasive pre-preparation of joint surfaces or removal of bone, which is thereby preserved in an effort to facilitate future surgery should it be necessary and to enable the patient to take advantage of newer technology or progression of treatments regimen, e.g., allowing for future revision.

Yet another advantage of the present disclosure (as compared with more radical or open therapies, e.g., total joint replacement) is that the procedure may also be readily performed; as an adjunct to other procedures, such as instrumented fusion and disc replacement. This is advantageous given the kinematic and biomechanical interdependence of facet joints and intervertebral discs including vertebral motion segments, that in turn give rise to a risk of co-morbidity facets (for example, it is believed by many clinicians of skill in the art that facet degeneration is exacerbated as a result of total disc replacement procedures, such that replacement of the disc without concomitant therapy of diseased facet joints will result in failure of the prosthesis).

Still another advantage of the methods and apparatus of the anchored articulating implant assemblies of the present disclosure is that the resurfacing provided is anatomically and biomechanically more similar to the natural joint, as compared with total joint replacements, resulting in increased stability, flexibility and range of motion.

Unlike total joint replacements which may impart shear and strain forces upon the facet joint, the implant assemblies of the present disclosure neither impart shear forces nor constrain shear movement of the joint, nor constrain lateral rotation or lateral bending. The methods and instrumentation systems of the present disclosure facilitate deployment of the therapeutic anchored articulating implant assemblies with precision and in an aligned orientation to enable them to augment and restore the natural joint structures which bear physiologic loads, in line of principal compressive stress. Additionally, in one example, the spinal joint resurfacing devices of the present disclosure utilize a metal-metal bearing rather than the metal-polyethylene bearings that are often utilized in other articulating joints (e.g., knees; hips). Metal bearings have demonstrated a much higher level of wear resistance as well as reduced bone loss and inflammatory tissue reaction about the joint as compared to metal-polyethylene bearings, so that these factors individually and collectively enable the implant assemblies of the present disclosure to not only restore motion, but further, motion is preserved by minimizing ongoing inflammation and degeneration.

Yet another aspect and advantage of the methods of deployment of the present disclosure is that, as no capsule tissue is removed, and piercing of the joint capsule is minimal, little leakage of synovial fluid occurs, and the introduction of the spinal motion preservation assembly of the present disclosure is accomplished without the need to surgically create or otherwise deleteriously enlarge a hole in the joint.

A further advantage of the methods and spinal mobility preservation assemblies of the present disclosure is that since therapies are provided without the removal of joint capsule tissue, and the area being re-surfaced is substantially cortical bone which has very little vascularity, there is minimal impact on periosteum and cancellous bone, both of which have much greater blood supply. Thus, the methods of the present disclosure provide spinal therapy that minimizes tissue disruption and exposure to blood in the surgical field, which exposure could otherwise promote unwanted bone growth and eventual fusion.

In addition to being less invasive, yet another advantage of the methods, instrumentation systems, and apparatus of the present disclosure for dynamic spinal stabilization is that the percutaneous, posterior approach obviates the necessity for, and trauma from, sectioning or releasing major muscle groups that stabilize the joint during flexion, extension, and rotation. The therapies of the present disclosure are generally provided as an outpatient procedure in substantially about 30 minutes in some embodiments. So, as compared with current procedures, in addition to reduced blood loss as previously noted, there are other concomitant advantages afforded by the present disclosure, including, but not limited to, reduced time under anesthesia; reduced morbidity and post operative infection; and reduced recovery time. By obviating the prolonged convalescence and surgical complications of more invasive procedures, and by providing positive clinical outcomes, the methods and apparatus of the present disclosure benefits the patient, the surgeon, and the health care system in terms of the reduction in financial impact on health care insurers, and disability and workers' compensation providers.

Another advantage is that risks associated with implant expulsion, migration, or subsidence are inherently and substantively less for the spinal motion preservation assemblies of the present disclosure, mitigated by implant retention fixtures, e.g., by external, self-tapping threads configured to distribute stress evenly over a large surface area, that engage the joint and secure (i.e., anchor) the implant assemblies therein.

Other systems, methods, features and advantages of the disclosure will be or will become apparent to one with skill in the art upon examination of the following figures and detailed description. It is intended that all such additional systems, methods, features, and advantages be included within this description, be within the scope of the disclosure, and protected by subsequent claims.

BRIEF DESCRIPTION OF THE DRAWINGS

The present disclosure will now be illustrated more fully with reference to accompanying drawings in order to disclose selected exemplary implementations of the present disclosure. The teachings of the present disclosure may, however, be embodied in many different forms and should not be construed as limited to the particular implementations set forth herein; rather these implementations are provided so that the disclosure can be thorough and complete, and as part of the effort to convey the scope of the disclosure to those skilled in the art.

DETAILED DESCRIPTION

The following detailed description of the methods and apparatus of the disclosure is useful to an understanding as to how the inventive therapies overcome disadvantages of all known devices by providing a novel device which enables replacement of degenerated articular surfaces with articular prostheses that cancel bone-cartilage frictions of degenerated surfaces, and therefore pain and/or osteophytic induction with nerve root compressions in foramenae, while preserving unconstrained vertebral motion.

In order to provide an overview of the components and their placement with respect to a spinal motion segment, the explanation will start with a description of an implant assembly, followed by descriptions of an exemplary instrumentation system and a method of use for inserting exemplary prostheses. Subsequent drawings will provide additional detail on the assembly and delivery of the device. In general terms, however, systems or kits in accordance with the present disclosure can include one or more implant assemblies, along with one or more of a guide wire, a dilator, a cannula, a drill, a tap, and a driver/introducer, each of which are described below.

Implant Assembly

In one aspect of the disclosure, spinal motion preservation prosthetic device is provided that "replaces" a native joint surface with a metal-on-bone liner on at least one of two articulating joint surfaces.

For convenience, as described herein the components of the motion preservation assembly include a superior segment (anchored in the "half" of the facet joint that is the inferior articular process of the more cephalad vertebral body in the motion segment targeted for treatment) and an inferior component (anchored in the "half" of the facet joint that is the superior articular process of the motion segment's more caudal adjacent vertebral body).

Figure 1:
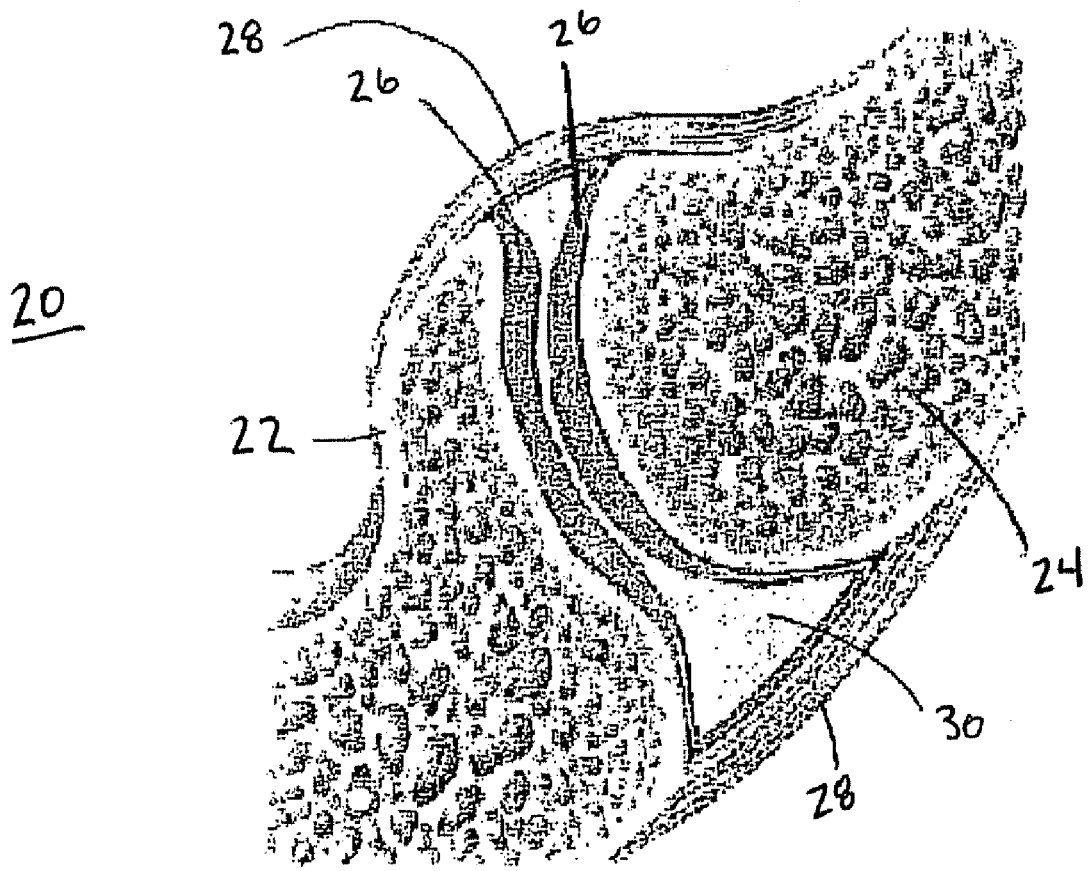
FIG. 1 is an enlarged, simplified illustration of a facet joint with which the devices, kits, and methods of the present disclosure are useful in treating.
Figure 2:
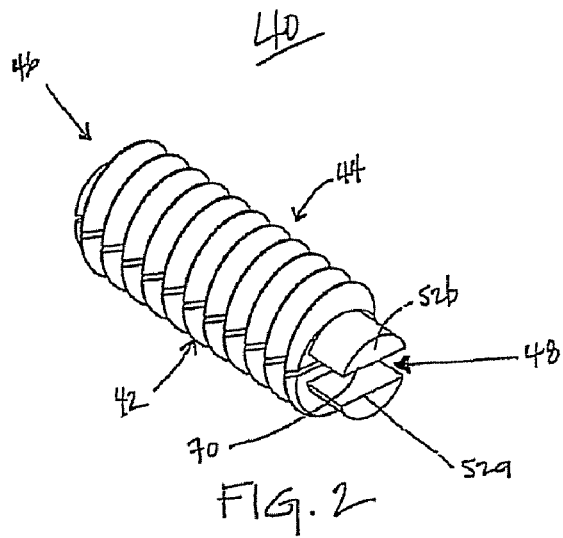
FIG. 2 is a perspective view of an implant assembly in accordance with principles of the present disclosure.

In accordance with some aspects of the present disclosure, and with reference to FIG. 2 an exemplary facet resurfacing implant or device is provided as an implant assembly 40 generally including at least two components, a superior implant component 42 that serves as a liner for a superior facet joint articulating surface, and an inferior implant component 44 that serves as a liner for an inferior facet joint articulating surface, of an adjacent pair of vertebral facet joints, i.e., between a superior articular facet of a selected vertebra and an inferior articular facet of a vertebra immediately above the selected vertebra.

Specifically, the prosthetic liner or implant assembly 40 is generally configured such that each implant component 42, 44 indirectly or optionally directly mates to the other (e.g., as a longitudinally cross-sectioned half of a whole) to define a leading end 46 and a trailing end 48 of the implant assembly 40. In some constructions, and the superior facet implant component 42 and the inferior facet implant component 44 are highly similar, each constructed as an elongate, hemi-spherical rod fabricated from, for example, cobalt-chrome alloy or such other high tensile strength, wear-resistant, biocompatible metal or metal alloys, as will be described below, appropriate for joint resurfacing, and it is generally preferred that the liner components 42, 44 be constructed from the same material, in view of wear and abrasion resistance considerations. The components 42, 44 combine to form a more continuous rod-like structure upon final construction as the implant assembly 40.

Figure 3A:
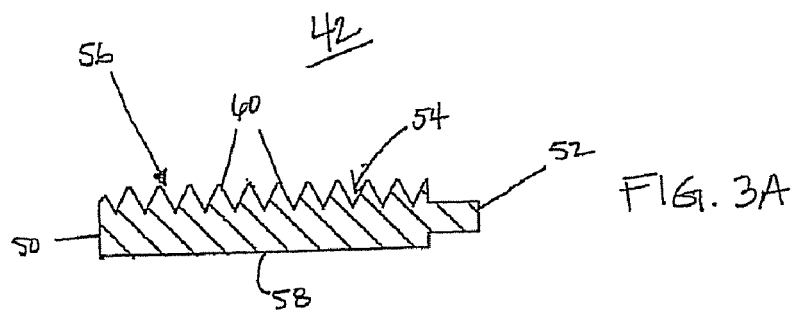
FIG. 3A is a side view of a superior facet implant component of the assembly of FIG. 2.
Figure 3B:
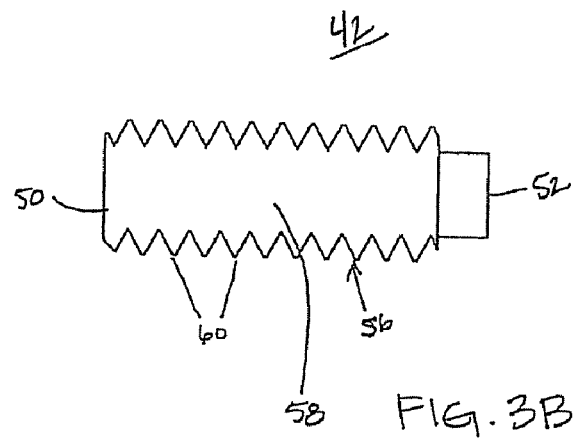
FIG. 3B is a bottom view of the component of FIG. 3A.
Figure 3C:
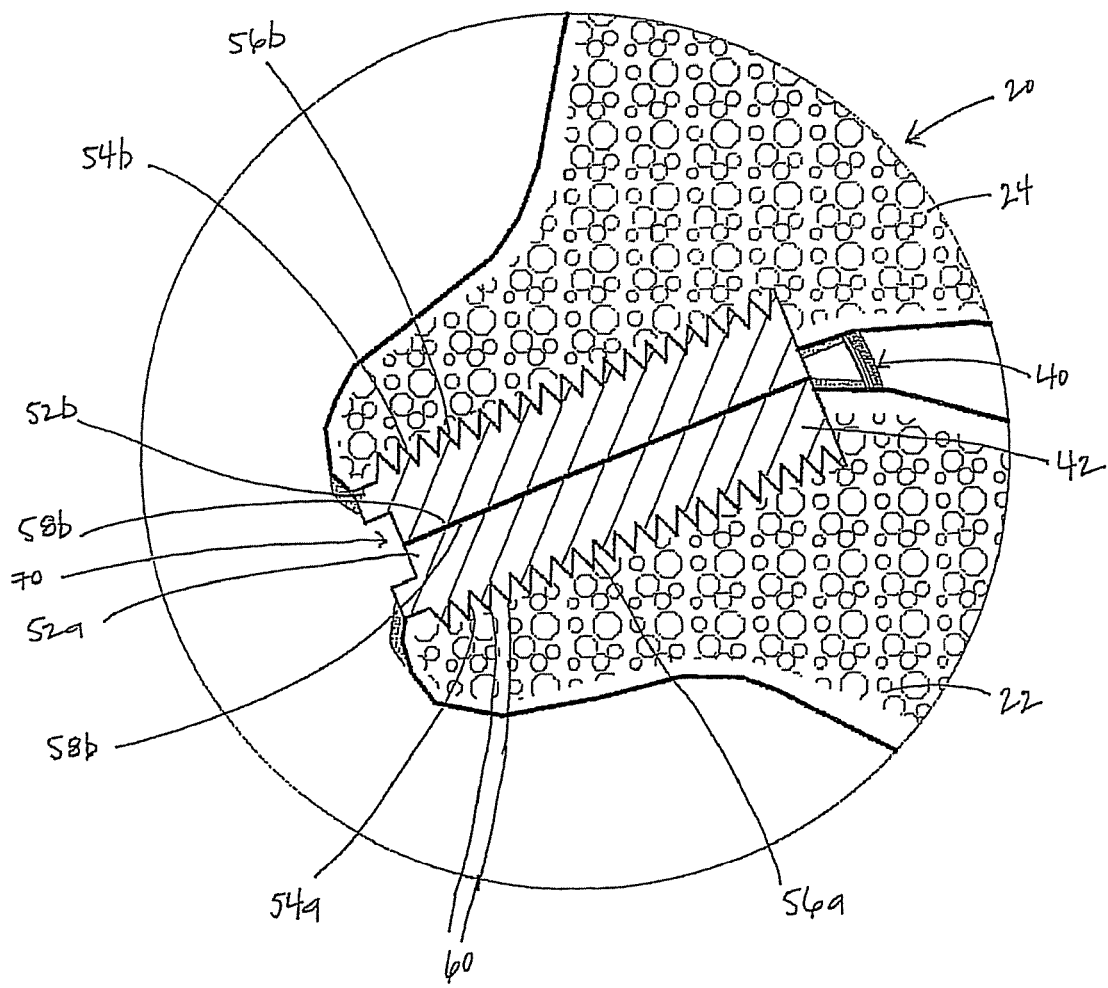
FIG. 3C is a simplified illustration of the implant assembly of FIG. 2 inserted within a facet joint.
Figure 3D:
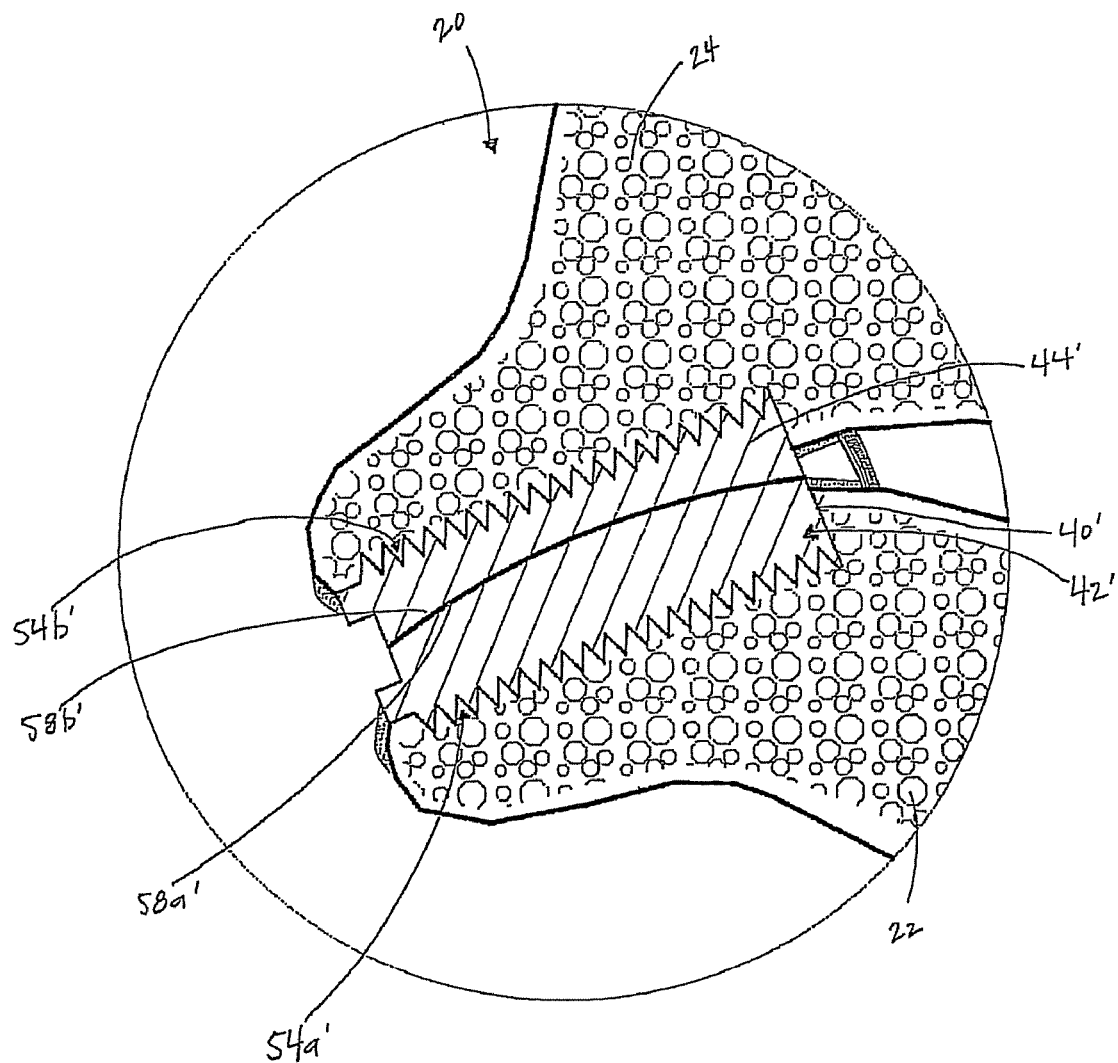
FIG. 3D is a simplified, cross-sectional view of an alternative implant assembly in accordance with principles of the present disclosure inserted within a facet joint.

More specifically, FIGS. 3A and 3B illustrate the superior facet implant component 42 in isolation, it being understood that the inferior facet implant component 44 can be similarly construed. The implant components 42, 44 are each configured to include or define opposing ends 50, 52, and a first surface 54, e.g., a cylindrical-like surface, which includes an anchoring feature 56 to engage with, and affix the prosthetic device 40 (FIG. 2) into, the bone of the native articulating surface of the targeted facet joint. Affixment of the components 42, 44 in the form of implant assembly 40 within the facet joint 20 is shown in FIG. 3C with features of the superior component 42 labeled with the suffix "a" and features of the inferior component labeled with the suffix "b". Opposing the first anchoring surface 54 is a second surface 58 which may be linear (axial) as shown, or it may be curvilinear (for example, as shown in FIG. 3D relative to an alternative implant assembly 40' inserted to the facet joint 20) and serves as a prosthetic articulating surface. As illustrated in FIGS. 3A and 3B, the articulating surfaces 58a, 58b are both planar across a width of the implant components 42, 44 that extends between opposing sides of the implant component 42, 44. As identified in FIG. 3C, when the implant assembly 40 is deployed into the facet joint 20, the articulating surface 58a of the superior facet implant component 42 and the articulating surface 58b of the inferior facet implant component 44 of the implant assembly 40 abut, one against the other, so that these surfaces 58a, 58b are in lateral sliding engagement along substantively the length of the articulating surfaces 58a, 58b, but are precluded from rotational misalignment (as sometimes occurs with "floating" implants) due to the fact that the respective superior facet implant and inferior facet implant components 42, 44 are anchored in the joint bone, with anchor method and fixtures as will be described below.

As a point of reference, when the implant assembly 40, 40' is inserted into the articular space it also serves as a joint spacer that dilates the joint by maintaining height between the superior and inferior facet; distracts and decompresses the motion segment, thereby providing pain relief, and in accordance with one aspect of the disclosure, the implant assembly 40, 40' may be varied somewhat in size (rod diameter) to achieve a desired level of distraction, for example from between about 0.1 mm and about 4 mm, often about an additional 1 mm increase in joint separation, which is somewhat dependent on anatomy and availability of bone stock. Additionally, it is generally intended that the anchoring surfaces 54 of the implant assembly 40, 40' be secured into the bone as deeply as possible, so typically the spacer depth accountable for the increase in separation will be substantially attributable to the overall dimensional depth of the two mating articulating surfaces, i.e., the superior implant articulating surface 58a in contact with the inferior implant articulating surface 58b.

In general, the nature and configuration of the anchoring feature 56 will depend at least in part on the location, amount, and condition of bone stock available for securing the prosthesis 40, 40' to the joint. In certain examples, the anchoring feature 56 for engagement of the anchoring surface 54 of the each of the superior facet implant and inferior facet implant components 42, 44 of the implant assembly 40 with the bone of the articulating surface of a joint may be configured to include posts, flanges, barbs, or other suitable features or bone cements (e.g., PMMA, and the like), or combinations thereof, used and known in the art to secure metal-to-bone.

In an exemplary example (shown), the anchoring method for engagement of the anchoring surface 54 of the each of the superior facet implant and inferior facet implant components 42, 44 of the implant assembly 40 with the bone of the articulating surface of a joint include external bone threads 60, cut "like-handed" into the cylindrical surfaces 54 of the rod-like implant assembly 40.

The screw threads 60 are typical of cortical type bone threads known in the art, i.e., of a finer pitch and shallower thread depth than those of cancellous bone threads. In one example, the threads are cut as M5×1 threads, (i.e., 5 mm in diameter with 1 mm spacing between threads). In another example, threads 60 are cut with generally flat faces on the flights of the thread 60 with the most flat of the faces oriented in the direction of the applied load. In yet another example, the thread 60 profile consists of flights with an asymmetric thread form, which provides the advantage of improved weight bearing and load distribution. In fabrication, and returning to FIG. 2, threads 60 are formed on root portions of the anchored articulation assembly 40 and extend as continuous threads from the trailing end 48 to the leading end 46. The screw threads 60 include multiple revolutions that are spaced apart along the roots by inter-thread spacings. The threaded implant assembly 40 is configured to be able to withstand sufficient applied torque without bending or buckling during insertion into the joint cortical bone; the rod-like shape of the implant assembly 40 is between about 5 mm and about 30 mm, and optionally about 15 mm in length, with a rod outer diameter of between about 3 mm and about 10 mm, optionally about 5 mm. Installation is simplified by pre-loaded delivery of the two bone anchor components 42, 44 (i.e., FIG. 3C illustrates the anchoring surfaces 54a, 54b of the corresponding superior and inferior components 42, 44 are affixed to the native bone of the inferior and superior facet articulating surfaces 22, 24) via "timed" delivery of the threaded components 42, 44; thus the threads 60 are also cut like-handed in relation to other tools included in the instrumentation system of the present disclosure, e.g., a tap, and an introducer driver-introducer tube assembly used in the insertion of threaded implant assemblies, as will be described in more detail below.

In the context of the present disclosure, as used herein the implant assembly 40 includes the leading end 46 for insertion first into the joint space, and the trailing end 48 opposite the leading end 46, and therebetween a length along a longitudinal axis of the implant assembly 40. The leading end 46 is more distal to the operator than the trailing, or proximal, end 48.

In one example, the leading end 50a or 50b of one or both of the superior component 42 and the inferior component 44 may be configured to include a chip breaker (not shown) to assist in cutting a thread path that is not pre-threaded. A chip breaker is a discontinuity in the thread 60 that allows chips to break off as the thread path is cut. More specifically, an implant assembly configured with a leading end 46 that includes a chip breaker is deployed either directly into bone, or into a pilot channel (the purpose and formation of which will be described below) that has been drilled, but not tapped, into the bone. In the context of the present disclosure, it will be understood that the terms pilot "channel", "hole", and "bore" may sometimes be used interchangeably. Moreover, an implant assembly configured with a leading end that includes a chip breaker will generally also be configured to include self-drilling, as opposed to self-tapping, threads.

With reference to FIGS. 2 and 3C, the trailing end 52a of the superior facet component 42 and the trailing end 52b of the inferior facet implant component 44 of the implant assembly 40 are configured to form, when assembled, a female engagement fixture 70 (e.g., slot, square, hex, etc.) that releaseably mates with a male engagement fixture (e.g., blade, square, hex) included in an introducer driver sub-assembly that is configured to insert the spinal motion preservation implant assembly into the facet joint 20, which insertion method will be described in greater detail below. In one example, the female engagement fixture 70 is configured as a slot that receives male engagement fixture configured as a flathead driver. Alternatively, the respective female-male engagement fixture can assume other forms such as a hex-head configuration.

As reflected by the alternative implant assembly 40' of FIG. 3D, in other embodiments, the superior component 42' and the inferior component 44' are configured to provide the implant assembly 40' with the articulating surfaces 58' are curvilinear in more than one plane, i.e., along and across the longitudinal axis, to enable rotational articulation to match the radii of curvature of the joint targeted for therapy, e.g., shaped to conform with the specific anatomy of the facet joint 20, which will vary with spinal level.

For example, with respect to a curvilinear as opposed to an axially linear articulating surface, the inferior component 44' implant articulating surface 58b' may be configured such that it acts as a "female" surface wherein it is concave or configured to be accepted by a "male" (e.g., convex) articulating surface 58a' of the superior implant component 42'. Conversely, the inferior implant component 44' articulating surface 58b' may also be configured such that it acts as a "male" surface wherein it is configured to accept a "female" articulating surface 58a' of the superior implant component 42'. Configuring the components 42', 44' to maximize the surface area of contact between articulating surfaces will maximize load bearing.

As implantable components, the assemblies 40, 40' can be fabricated from biocompatible orthopedic implant materials that are common medical grade materials, i.e., with substantial clinical history across a wide variety of orthopedic utilities that present no biocompatibility issues. In the context herein, "biocompatible" refers to an absence of chronic inflammation response when or if physiological tissues are in contact with, or exposed to (e.g., wear debris) the materials and devices of the present disclosure.

In addition to biocompatibility, in another aspect of the present disclosure, the material(s) selected for the implants are sterilizable; visible and/or imageable, e.g., fluoroscopically; or via CT (computed tomography), or MRI (magnetic resonance imaging), with this last-named imaging technique mandating that materials be substantially free of iron. More specifically, the components 42, 44 are formed (machined, following heat treatment of blank rod), from high tensile strength (greater than substantially from between about 250 Kpsi to about 300 K psi), high fatigue strength metal alloy rod, preferably not containing Fe, such as titanium materials meeting standards (e.g., ASTM F136) typical in the art for surgical implant applications. Wrought, extra low interstitials (ELI) titanium-6 aluminum-4 vanadium alloy (Ti6Al4V) is a candidate material, and other candidate materials may be selected from among, for example, high strength (e.g., high tensile strength, high fatigue strength), wear and abrasion resistant metal alloys (e.g., MP35N; Elgiloy™, a super alloy of cobalt chrome; Co—Cr alloy such as Stellite™; or non-magnetic, Ni—Co—Cr—Mo alloy available from Carpenter Technology Corporation, Reading, Pa., and nitride-coated Ti alloys) according to the desired biomechanical properties.

In addition, implant component surfaces 58, 58' may undergo additional treatments to optimize performance. For example, articulating surfaces 58, 58' may be mechanically or chemically polished, coated (e.g., Ti-nitride), or heat or surface treated to improve wear and abrasion resistance, or coated to enhance lubricity or hydrophilicity. Anchoring surfaces 54, 54' may be ion-bombarded, sputter coated, or otherwise treated to enhance porosity and promote bone ingrowth, or coated with substances that promote bone growth, e.g., coated with hydroxyapatite. It will also be understood by those of skill in the art that such treatments may be used individually, or in combination thereof, as indicated and appropriate.

In further embodiments, one or more surfaces of a facet prosthesis 40, 40' may be covered with various coatings such as antimicrobial, antithrombotic, and osteoinductive agents, or a combination thereof.

Instrumentation System

The implant assemblies 40, 40' of the present disclosure can be delivered to, and inserted within, the facet joint 20 in a variety of manners via various instrumentation sets or systems. As used in this disclosure, for convenience with respect to instrumentation descriptions it will be understood that the terms "distal" and "proximal" are defined in context of a clinician holding the device in its typical operative orientation, wherein a distal end (e.g., instrument tip) is more distant from the user, while a proximal end is closer to the user (e.g., where held or where there is an instrument handle).

With respect to handles, in accordance with one aspect of the present disclosure, for operative convenience in handling or in applying torque, where appropriate, the proximal ends of certain instruments, as will be described below, are configured to engage a handle. The handle may be formed from among one of several materials that are sterilizable and of suitable mechanical properties (e.g., tensile strength; impact resistance), for example machined from a metal alloy, such as medical grade stainless steel, or fabricated from a suitable polymeric material that is machined or injection-molded, for example, Kynar® high molecular weight crystalline thermoplastic polymer of vinylidene fluoride (polyvinylidene fluoride or PVDF), or Delrin™ acetal-copolymer. As functionally appropriate, handles may be configured as turn knobs, or "T" handles, and may be releasably affixed, such as by threaded engagement with proximal ends of instrument shafts, or if permanently attached then preferably by mechanical pinning or welding, soldering, brazing, gluing or other suitable securing or fastening methods. As functionally necessary, handles may also be cannulated to permit passage of an instrument over a guide wire.

Guide Wire

Figure 4A:
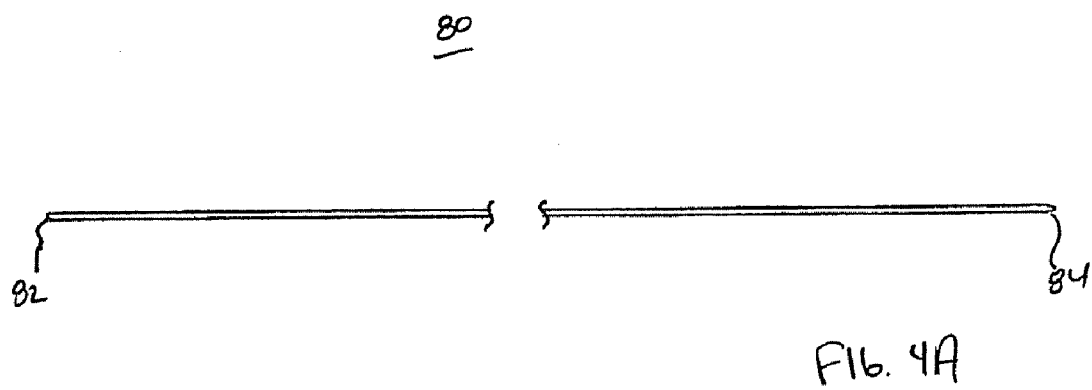
FIG. 4A is a side view of an optional guide wire useful with kits and systems in accordance with the present disclosure.
Figure 4B:
FIG. 4B is an end view of the guide wire of FIG. 4A.

One optional tool useful with kits and system of the present disclosure is a guide wire 80 shown in FIGS. 4A and 4B. As used herein, in the context of the present disclosure, the terms guide pin, guide wire and K-wire (i.e., Kirschner wires) are sometimes used interchangeably.

The guide pin 80 can be fabricated from a suitable, medical grade metal alloy (e.g., series 300 stainless steel) rod that is configured as an elongate body with a proximal end 82 and a tapered distal end 84 (i.e., a pointed tip enables it, when tapped, to pierce the joint capsule and enter). Ranging from between about 0.5 mm to about 4 mm, and optionally about 1 mm in diameter, and between about 150 mm to about 500 mm, and optionally about 305 mm in length, the guide pin 80 may be used to locate and literally "pinpoint" a target site for therapy. The guide wires assist in the establishment of a relatively minimally invasive percutaneous access channel through soft tissue or bone, which is created by the subsequent insertion over the guide wire of a dilator or series of dilators, as will be described in greater detail below.

More specifically, one option is to use the guide wire 80 to assist intra-operative placement of cannulated instruments and other devices into the surgical field. For example, as will be described in more detail below, cannulated drills and taps are inserted over the guide wire 80 (of about 1 mm in diameter) and into and through a working cannula to the surgical field where they are used, respectively, to create and pre-thread at least one pilot bore in preparation for the subsequent insertion of the prosthetic implant assemblies of the present disclosure.

In the context of the present disclosure, the terms pilot bore, hole and channel are used interchangeably.

Dilator and Dilator Sheath

Figure 5A:
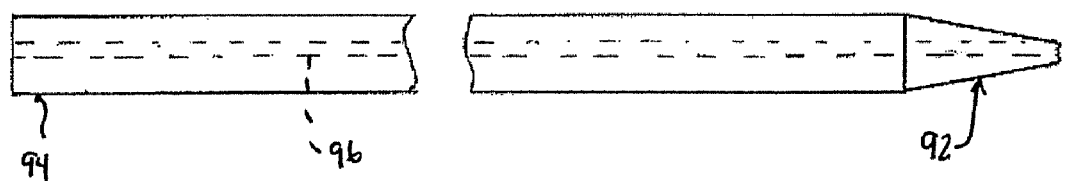
FIG. 5A is a side view of an optional cannulated dilator useful with kits and systems of the present disclosure.
Figure 5B:
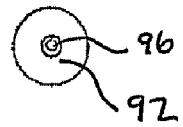
FIG. 5B is an end view of the dilator of FIG. 5A.

Another optional tool useful with kits and systems of the present disclosure is one or more cannulated dilators 90 shown in FIGS. 5A and 5B. The cannulated dilator 90 can be fabricated from sterilizable, medical grade metal alloy (e.g., series 300 stainless steel rod) or polymer, is configured as an elongate body having a conical and tapered distal end 92, a proximal end 94, and a central lumen 96 within and along the longitudinal axis of the dilator 90 that enables the distal end 92 of the dilator to be inserted and delivered over a guide wire (e.g., the guide wire 80 of FIG. 4A), for delivery in combination and as part of an assembly with the guide wire to the target site, where the distal end 92 is docked into the joint, e.g., by striking its proximal end with a mallet or hammer.

In one example of the present disclosure, the cannulated dilator(s) 90 is from between about 100 mm to about 400 mm, and optionally about 265 mm in length, with a taper starting from about 13 mm proximal of a distal tip 98 in some embodiments; with an outer diameter of between about 3 mm to about 10 mm, and optionally about 6 mm; an inner diameter that is slightly larger than the outer diameter of the guide wire 80 (FIG. 4A), such that for a 1 mm guide wire 80 the inner diameter of the cannulated dilator 90 is optionally about 1.5 mm. The dilator 90 serves to dilate soft tissue and bone, to atraumatically establish a percutaneous access tract which extends from a point external to the patient, and through the patent's skin to the target site.

Figure 6A:
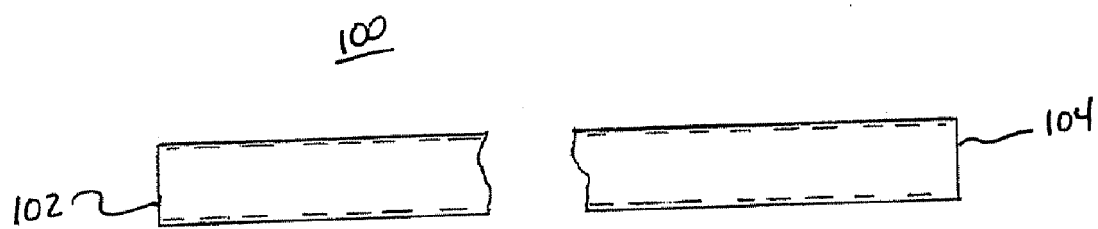
FIG. 6A is a side view of an optional sheath or cannula useful with kits and systems of the present disclosure.
Figure 6B:
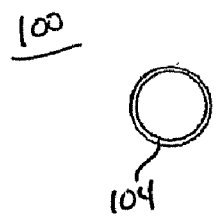
FIG. 6B is an end view of the sheath of FIG. 6A.

With reference to FIGS. 6A and 6B, an optional cannulated dilator sheath 100 is further provided and is fabricated from sterilizable, medical grade metal alloy (e.g., series 300 stainless steel) tubing. The sheath 100 is configured as an elongate body including a proximal end 102 and a distal end 104. The dilator sheath 100 is configured to slide and fit concentrically over the cannulated dilator 90 (FIG. 5A), and thus the inner diameter of the dilator sheath 100 is slightly larger than the outer diameter of the cannulated dilator 90. More specifically, the distal end 104 of the dilator sheath 100 is passed over the dilator 90 guide wire 80 assembly and advanced distally to the target site where the distal end 104 of the dilator sheath 100 is docked into the joint over the dilator 90 (if necessary, including tapping the proximal end of the sheath of cannula 100 with a mallet). Following removal of the cannulated dilator 90 from the surgical site (generally performed by twisting the proximal end 94 of the dilator 90 and pulling it in a proximal direction back over the guide wire 80), the dilator sheath 100 subsequently serves as a portal through which site access and preparation tools and prosthetic devices, such as the anchored articular assemblies 40 (FIG. 2) of the present disclosure, are deployed to the surgical site, and in context, it will be understood that the terms "dilator sheath" and "working cannula" are sometimes used interchangeably. Thus, the inner diameter of the working cannula 100 must also be slightly larger than, and accommodate the outer diameters of, the instrumentation and implant assemblies 40 which are deployed to the surgical site through this protected portal. Similarly, it will be understood that the lengths (dimensions of longitudinal axis) of certain tools (e.g., drill; tap) in the instrumentation system of, the present disclosure will be inter-dependent with, and configured in consideration of the length of the working cannula 100.

More specifically, in one example of the present disclosure, the dilator sheath 100 is from between about 100 mm to about 500 mm, and optionally about 230 mm in length; has an outer diameter of between about 4 mm to about 12 mm, and optionally about 7 mm; an inner diameter that is slightly larger than the outer diameter of the dilator 90 (FIG. 5A) over which it is concentrically fit, such that for dilator of about 6 mm in diameter, the dilator sheath 100 is optionally about 6.6 mm, and with a tube wall thickness of between about 0.2 mm to about 1 mm, and optionally about 0.5 mm.

In one aspect of the present disclosure, the dilator 90 (FIG. 5A) and dilator sheath 100 are inserted as an integral assembly, and may be deployed by a removable and cannulated handle (not shown) on the proximal end 102, e.g., fabricated from materials such as noted in the description of the handles configured on the proximal ends of drill and tap, below.

Drill

Pre-drilling for the implant assembly 40 (FIG. 2) deployment is generally indicated, and thus is useful for self-tapping threads (versus self-drilling threads). Also, the harder the bone, the more beneficial it may be to pre-drill, to perforate the cortical bone while controlling the applied force, feed rate, and amount of heat generated (i.e., drilling in bones requires energy and part of the energy is lost as heat), so as to preclude thermal necrosis of the bone. However, if a channel is not drilled, the implant assembly 40 may strip its threads during its insertion through the cortical bone, resulting in diminished purchase or anchoring.

Figure 7A:
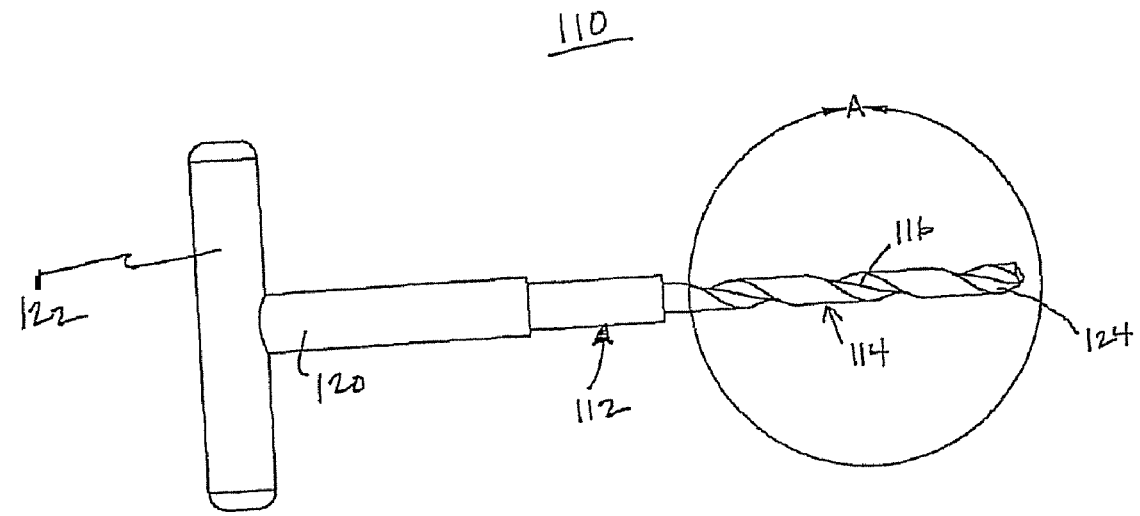
FIG. 7A is a side view of an optional drill useful with kits and system of the present disclosure.
Figure 7B:
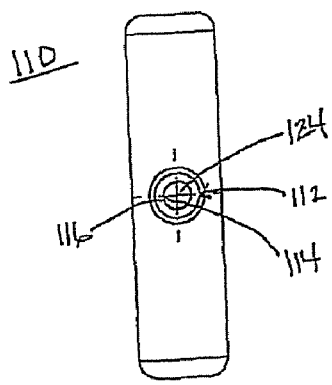
FIG. 7B is an end view of the drill of FIG. 7A.
Figure 7C:
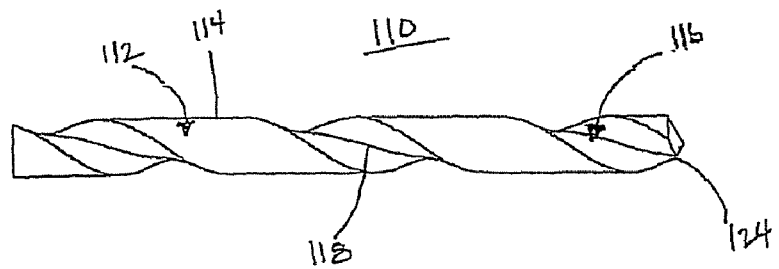
FIG. 7C is an enlarged view of a distal portion of the drill of FIG. 7A.

With the above in mind, another optional tool useful with kits and systems of the present disclosure is a drill 110 shown in FIGS. 7A-7C. The drill 110 is generally configured as an elongated rod (or shaft) 112 having a distal end 114 including a fluted section 116 with helical flutes 118, and a proximal end 120 with a handle 122 attached thereto. In one aspect of the present disclosure, a tip 124 may first be advanced into the bone by impacting, e.g., with a mallet or hammer. The helical flutes 118 facilitate boring as the shaft 112 is turned (either manually or using a power appliance, depending on the configuration of the drill 110 used) in the appropriate direction— e.g., clockwise—to advance the drill 110 distally into the working channel extending beyond the distal end of the working cannula 100 (FIG. 6A) and into the joint to create a pilot bore. The drill rod 112 is typically fabricated from hardened stainless steel or the like.

More specifically, the drill rod 112 can be fabricated from, for example, a 300 series stainless steel (e.g., medical grade 304 or 316; full hard temper), and is sized to create a pilot hole slightly under the minor diameter and to a depth about equal to the length of the implant assembly 40 (FIG. 2). In one exemplary method of use, the drill 110 is passed through the extended working cannula 100 (FIG. 6A) to the target site (i.e., the joint receiving therapy). In an alternative example (not shown), the drill 110 is configured with the flutes 118 (i.e., cutting edges) and the distal end 114 being distally tapered, and the proximal end 120 engaged with the handle 122, with a length therebetween, and is cannulated throughout its length to permit delivery of the drill, over a guide wire (e.g., the guide wire 80 of FIG. 4A), to the target site. The dimensions of the drill rod 112 that is selected for use depend on operative technique used and target site, and to enable its insertion through the selected working cannula 100, thus may range from about 100 mm to about 500 mm and optionally about 300 mm in length; an outer diameter of between about 3 mm to about 10 mm, and optionally about 6 mm; and with a lumen diameter that permits its passage over the guide wire 80, such that for a 1 mm guide wire, a lumen diameter of optionally about 1.5 mm. The drill 110 is advanced by turning the handle 122 engaged at the proximal end 120 so that the cutting edge 116 at the distal end 114 of the drill 110 progressively bores into the bone, forming a bore that may be from between about 3 mm to about 10 mm in diameter, depending on the desired size of the implant assembly 40 to be deployed, which is determined and selected by the clinician based on the location of the joint receiving therapy and on patient anatomy.

Tap

Where the joint cortex is hard, in addition to drilling a pilot hole it may be necessary or beneficial to tap (pre-thread) the channel to facilitate subsequent safe insertion of implant assemblies 40 (FIG. 2) that include threaded anchors. By performing both drilling and tapping procedures, the ability of the anchor threads 60 (FIG. 2) to withstand greater torque is believed to be enhanced while at the same time reducing the torque required on the implant assembly 40 heads for deployment. That is, tapping may minimize failure due to torsional shear during insertion of the anchored articulation implant assembly into the joint, as well as minimizing the risk of cross-threading and of microfactures.

Figure 8A:
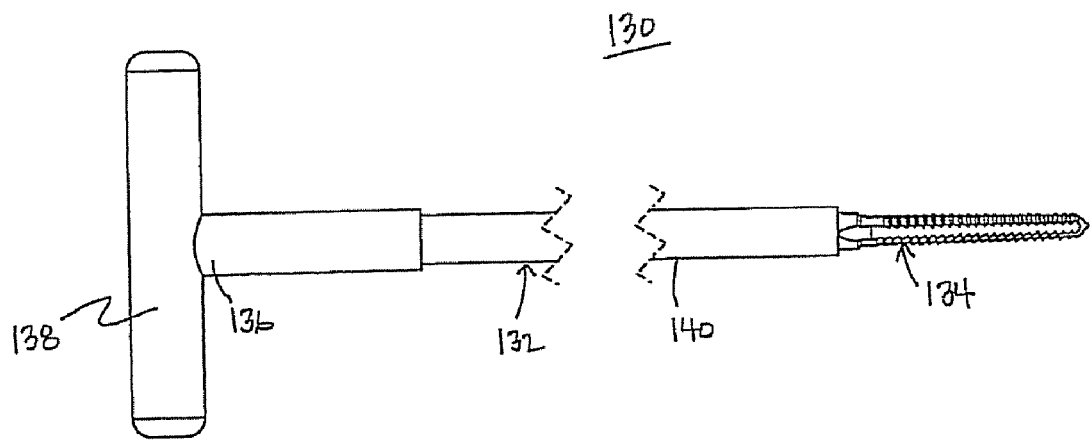
FIG. 8A is a side view of an optional tap useful with kits and systems of the present disclosure.
Figure 8B:
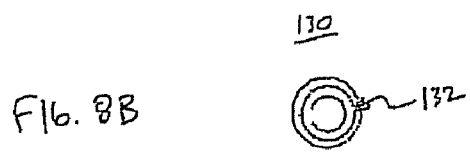
FIG. 8B is an end view of the tap of FIG. 8A.
Figure 8C:
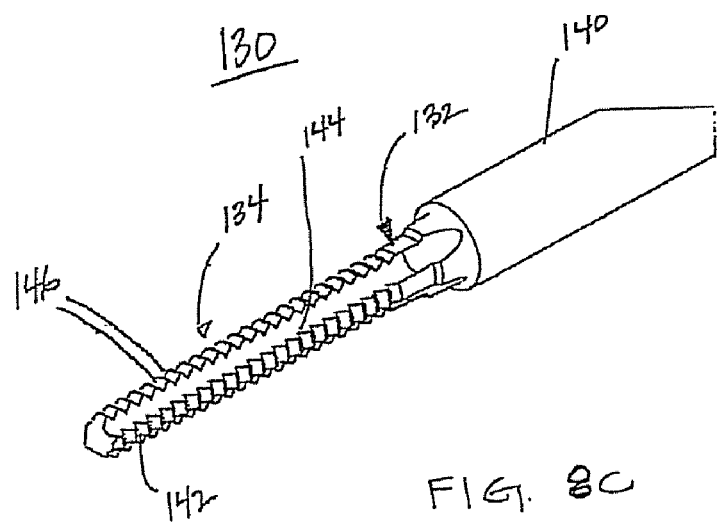
FIG. 8C is a perspective view of the tap of FIG. 8A.

With the above in mind, another optional tool useful with kits and systems of the present disclosure is a tap 130 shown in FIGS. 8A-8C. The tap 130 can be configured as an elongate shaft 132 with a threaded distal end 134, a proximal end 136 with a handle 138, and an intermediate segment 140 therebetween. In an alternative example, the tap 130 that is cannulated throughout its length to permit aligned delivery of the tap 130 to the target site over the guide wire 80 (FIG. 4A) and through the dilator sheath 100 (FIG. 6A). The cannulated tap 130 is configured to be able to apply sufficient torque to pre-thread the cortical bone of the pilot bore without bending or buckling. In addition, the surface of the distal end 134 includes a groove 142 with a recessed channel 144 (FIG. 8C) that minimizes channel backfill with tissue debris by facilitating the clearance of such debris created during tapping.

The tap 130 is typically fabricated from a hardened stainless steel (e.g., medical grade 17-4 alloy) and may be further enhanced with titanium-nitride (Ti—Ni) coated threads and flutes 146, and is generally selected/sized to tap (i.e., pre-thread) the pilot hole to slightly less than the thread (minor) diameter and to a depth about equal to the length of the implant assembly 40 (FIG. 2). The dimensions of the tap shaft 132 that is selected for use depend on operative technique used and target site, and to enable its insertion through the selected working cannula 100 (FIG. 6A), thus may range from about 100 mm to about 500 mm and optionally about 300 mm in length; an outer diameter of between about 3 mm to about 10 mm, and optionally about 6 mm; and with a lumen diameter that permits its passage over the guide wire 80 (by passing the distal end 134 of the tap 130 over the proximal end of the wire 80, and advancing the tap 130 distally) such that for a 1 mm guide wire, a longitudinal lumen diameter of optionally about 1.5 mm. The tap 130 is advanced into the pilot bore by turning the handle 138 engaged at the proximal end 136 so that the threads 146 at the distal end 134 of the tap 130 progressively advance into the bone, forming a thread path of size, pitch and "hand" that depends, as noted above, on the desired size of the implant assembly 40 to be deployed. Thus, in preparation for deployment of an exemplary implant assembly 40 the tap 130 used to pre-thread the pilot channel can be configured as a like-handed, 10-32 thread.

In one example, the tap 130 has between 1 and 4 flutes, often 2, and the flute length is longer than the thread length to facilitate chip removal, ranging from between about 10 mm and about 50 mm and optionally about 25 mm.

Driver-Tube Introducer Assembly

In another aspect of the instrumentation systems of the present disclosure, an introducer assembly used in the alignment and insertion of an anchored articulation implant assembly 40, such as shown in FIG. 3C, into the joint 20 targeted for therapy.

As will be described in more detail below, the introducer assembly includes a driver configured to engage and deploy the implant assembly 40, and a tube that is configured to fit concentrically over and engage with both the driver and the implant assembly 40, so that as the driver advances (torques) and orients the implant into the joint, the tube maintains the alignment of the separate component portions of the implant as they are inserted, i.e., precluding the superior facet implant and inferior facet implant parts of the prosthesis from shifting as they are threaded into the joint.

Figure 9A:
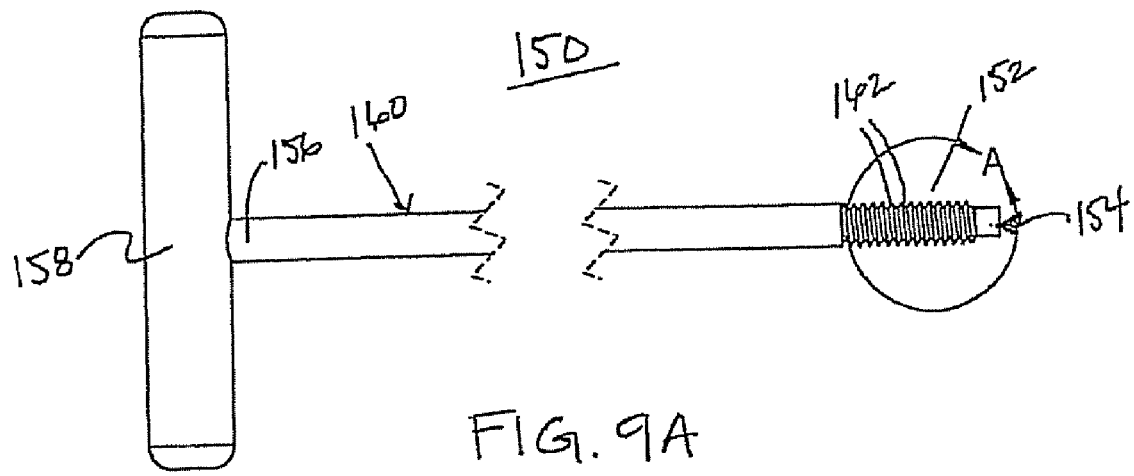
FIG. 9A is a side view of an optional driver useful with kits and systems of the present disclosure.
Figure 9B:
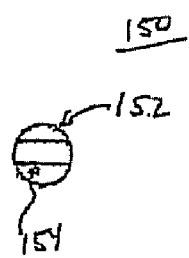
FIG. 9B is an end view of the driver of FIG. 9A.

With the above in mind, one example of a driver 150 useful with the present disclosure is illustrated in FIGS. 9A and 9B. The driver 150 is constructed as an elongate rod with a threaded distal end 152 that is configured at a tip 154 with a "flathead" driver-type projection, a proximal end 156 that engages a handle 158 that optionally includes indicia (not shown) to assist the operator in orienting the implant assembly 40 (FIG. 2), and an intermediate segment 160 therebetween. That is, during a surgical procedure, using the driver handle 158 indicia that are marked according to the orientation of the driver projection tip 154 in engagement with the implant assembly 40, a clinician can orient the introducer assembly-implant assembly to align and appropriately place the prosthetic articulating surface 58 (FIG. 2) or prosthetic bone attachment anchoring surface 54 (FIG. 2) on the target inferior or superior surface, depending on where attachment is desired against the target resurfacing bone. In addition, the handle 158 engaged to the proximal end 156 of the driver 150 serves as a "stop" to further distal advancement of the driver 150, following insertion and advancement of the distal end 152 of the driver 150 into and through a proximal end of an introducer tube as described below.

More specifically, the distal end 152 of the driver 150 includes external male threads 162, and is configured to engage internal female threads that are included within a distal end of the tube while the flathead projection (male) at the tip 154 is configured to engage a (female) slot formed by the "assembly" of the superior facet implant component 42 and the inferior facet implant component 44 when each half (FIG. 2) is pre-loaded into the driver-tube introducer assembly for subsequent insertion into the joint, as will be described in more detail below.

In one example, the driver rod 150 is typically fabricated from a hardened stainless steel (e.g., medical grade 17-4 alloy) with titanium-nitride (Ti—Ni) coated threads 162 that are sized in accordance with the introducer assembly tube threads (described below) and which in turn match the size of the threads of the selected implant assembly 40 (FIG. 2) to be deployed. Thus, in preparation for deployment of the implant assembly 40 shown in FIG. 3, and in conjunction with the introducer tube described below, the driver 150 used to torque the implant assembly 40 is configured as a like-handed, 10-32 thread.

The dimensions of the driver rod 150 that is selected for use depend on operative technique used and target site, and to enable its insertion through the selected working cannula 100 (FIG. 6A), thus may range from about 200 mm to about 500 mm and optionally about 300 mm in length, an outer diameter of between about 4 mm to about 6 mm.

Figure 10A:
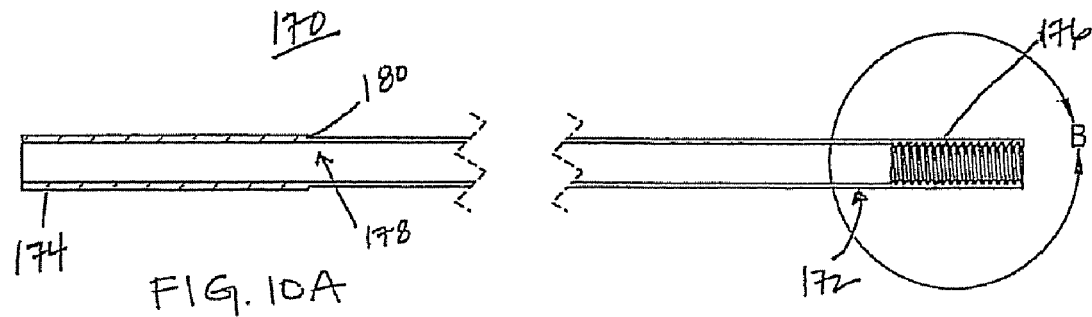
FIG. 10A is a side view of an optional introducer tube useful with kits and systems of the present disclosure.
Figure 10B:
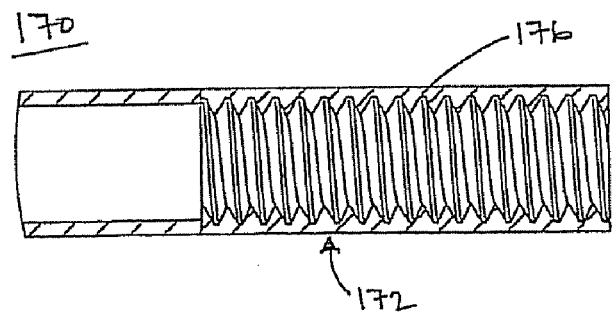
FIG. 10B is an enlarged, cross-sectional view of a portion of the tube of FIG. 10A.

An example of an introducer tube 170 is illustrated in FIGS. 10A and 10B. The tube 170 is constructed as an elongate body with a distal end 172 and a proximal end 174 with an intermediate segment therebetween. As noted previously, the distal end 172 of the elongate tube 170 is configured to include internal female threads 176 to threadably engage like-handed and sized external male threads both on the driver (e.g., the threads 162 in FIG. 9A), and those included on the implant assembly (e.g., the threads 60 in FIG. 2).

The proximal end 174 of the tube 170 is configured with a circumferential sleeve 178 that is inserted over and mechanically affixed (for example, by welding, soldering, or braising) to the tube 170 to form a shoulder 180 (i.e., a region of slightly larger outer diameter) that serves as a motion stop, such that when the leading or distal end of the pre-loaded implant assembly 40 (FIG. 2) introducer assembly unit is inserted into the working cannula 100 (FIG. 6A), it can be distally advanced until the shoulder 180 at the proximal end 174 of the tube 170 reaches the edge of the proximal end 102 (FIG. 6A) of the working cannula 100, whereupon due to constraints imposed by outer diameter, further distal advancement of the implant assembly 40 introducer assembly unit is stopped. As will also be described in greater detail below, it is from this pre-determined position, i.e., the location of the shoulder stop 180 on the tube 170 relative to the distal end of the (collective) introducer driver-implant assembly-working cannula, that the implant assembly 40 is advanced distally, by rotation of the driver 150 (FIG. 9A), to engage the pre-tapped channel into the joint.

In addition to dimensional considerations (i.e., relational shoulder stop-distal end separation as just described), the dimensions of the tube 170 that is selected for use also again depend on operative technique used and target site. The tube 170 is from between about 150 mm to about 400 mm and optionally about 230 mm in length with an inner diameter of between about 2 mm and about 5.5 mm, and with an outer diameter of between about 2.5 mm to about 6 mm for the segment of the tube 170 that is more distal to the shoulder stop 180, and an outer diameter of between about 7 mm to about 9 mm for the segment of the tube 170 that includes the sleeve 178. The sleeve 178 can be between about 5 mm to about 15 mm and optionally about 10 mm in length.

Methods of Access and Deployment

The assemblies, tools, and methods described in this disclosure are not limited to a specific method of access to the posterior of a motion segment facet joint. For example, as compared with therapies provided to lumbar facets, cervical facets may require a different operative approach (for example, posterior lateral approach versus a posterior approach) as well as modified access and preparation tools and implant assembly dimensions, because of coronal angulation. In addition, it will be understood that while for convenience the exemplary tools as described in this disclosure are generally linear and rigid, it is in fact anticipated that to facilitate certain joint therapies and operative approaches, some or all of the instrumentation system may be configured in whole or in part as needed and appropriate to be either or both curvilinear (e.g., the guide wire; working cannula), or flexible (e.g., drills or taps configured with flexible drive shafts). Such issues notwithstanding, those less familiar with the state of the art may benefit from an overview of one sequence of steps and tools that may be used to access and prepare the surgical site for subsequent deployment of an exemplary anchored articulating spinal motion preservation assembly. The following steps may be used to provide such access, preparation, and deployment.

In the methods and apparatus of the surgical systems of the present disclosure, precautions are indicated in access and preparation of surgical sites, including use of an imaging system, e.g., bi-planar fluoroscopy, to help maintain anterior/posterior and lateral alignment and facilitate surgery, and use of instrumentation with marking indicia in increments in mm as appropriate numbers to facilitate drilling or tapping accuracy, e.g., to preclude over-tap relative to the device to be deployed, and in particular with respect to the accurate placement and alignment of the prosthetic, anchored articulation assemblies within the joint.

Figure 11A:
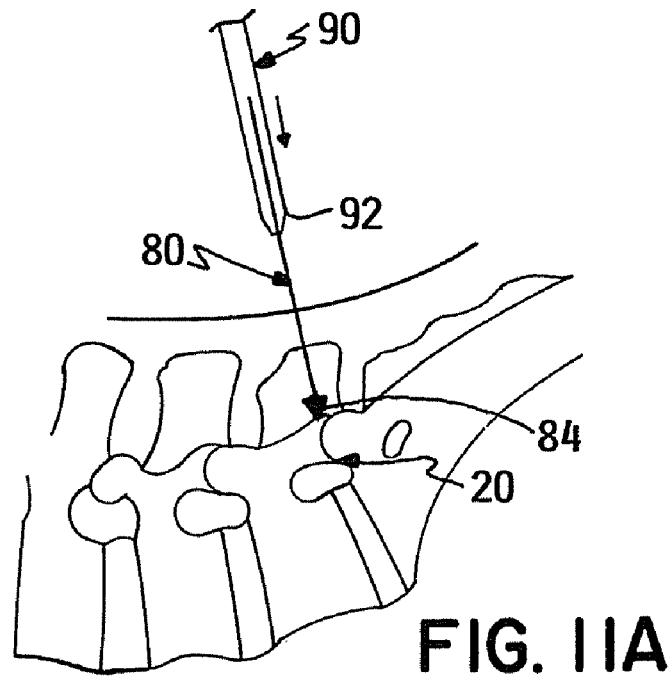
FIGS. 11A and 11B illustrate accessing an facet joint in preparation for subsequent implant assembly insertion into the joint in accordance with principles of the present disclosure.
Figure 11B:
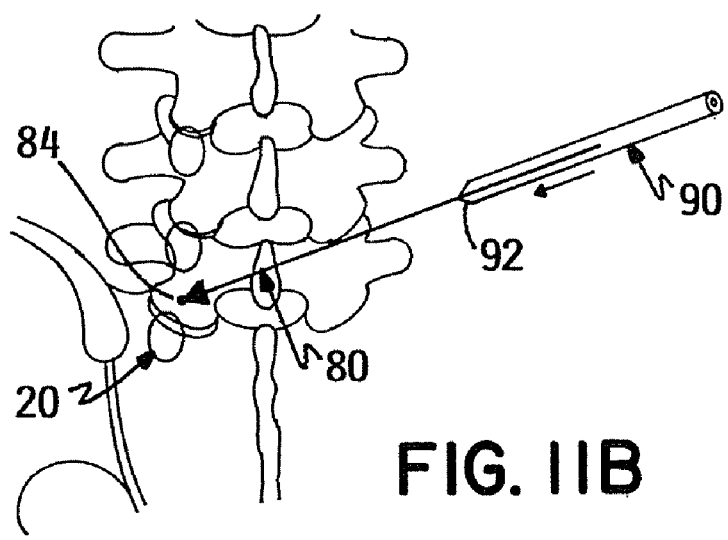

In one aspect of the present disclosure, the patient is placed in the prone position and X-ray imaging equipment is set-up to provide views in both the antero-posterior (AP) plane and the lateral plane so that the procedure can be performed under fluoroscopic guidance. With reference to FIGS. 11A and 11B, using fluoroscopy or image guidance, access to the facet joint 20 capsule and inter-articular space is achieved by advancing the guide pin/wire 80 through the soft tissue and docking the tip 84 of the wire/pin 80 into the facet space 20 at a point coinciding with an end of the joint's principal articulating axis. Contrast material may be injected to confirm guide pin 80 location, especially at first, but with experience, confirmation of appropriate pin placement can be made by feel and by viewing anteroposterior and lateral projections. Relative to the patient, it is typical for the clinician to work from cephalad to caudal in the lumbar spine, and caudal to cephalad in the cervical spine. The joint access tract formed between the point of skin entry, and docking at an end of the facet joint 20 may typically initiate one to two motion segment levels apart from the point of entry into the facet joint of the planned resurfacing to allow for optimal implant trajectory and placement. In patients with more advanced degenerative changes, osteophytes on the posterior facets may be removed to provide better visualization, to help define the anatomy of the facets, and to provide a suitable surface to allow for therapies as disclosed in this disclosure.

Access to and preparation of a posterior target site on the spine, such as the posterior of the L5-S1 segment facet joints, and subsequent deployment therapy, e.g., the anchored articulating implant assembly described above, may be performed following percutaneous entry, e.g., by means of a stab incision (the location of the incision may vary, dependent on individual patient anatomy), and by means of subsequent insertion of instrumentation systems including guide wires, dilators, cannulas, drills, taps, and driver-tube introducer assemblies, as described herein.

In this context of the present disclosure, the term percutaneous means through the skin from an access point on the patient and to the posterior target point, as in transcutaneous or transdermal, without implying any particular procedure from other medical arts. However, percutaneous is distinct from an open surgical access, and the percutaneous opening in the skin is preferably minimized so that it is less than 4 cm across, preferably less than 2 cm. The percutaneous pathway is generally aligned with the bore extending from the posterior target point through and into the joint and into the articular space, as visualized by radiographic or fluoroscopic equipment.

More specifically, the components and tools are introduced over the guide wire 80 which is often about 1 mm in outer diameter that is introduced via percutaneous insertion of the guide pin 80 performed by the clinician while using radiographic visualization, e.g., fluoroscopic guidance via both anteroposterior (AP) and lateral views to safely enable advancement of the guide pin through the soft tissue of the posterior access track up to and to locate the target site on a facet joint. Once the facet joint 20 is located, adjustments are made to achieve optimal trajectory through the joint capsule and into the articular space, which is again verified in both AP and lateral planes using the fluoroscope.

It will be understood that depending on the operative site and procedure, the method or order of insertion of the guide wire 80 and the dilator 90 may vary. For example, the guide wire 80 may be introduced via use of an introducer assembly, including a blunt tipped stylet, as is known in the art. The insertion and orientation of the guide wire 80 tends to be facilitated by a natural, "anatomic" pathway, typically the principal axis of articulation.

Figure 12A:
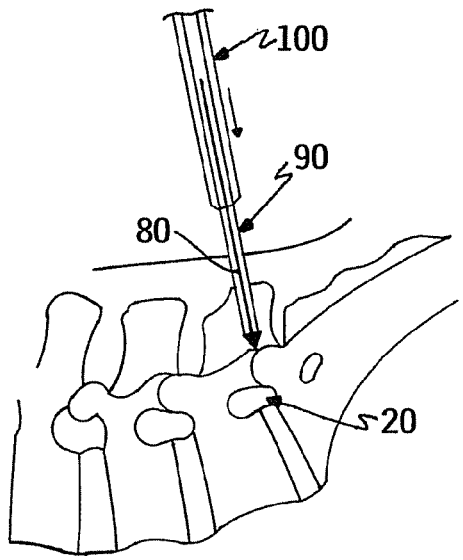
FIGS. 12A-12C illustrate use of the optional dilator and sheath instruments in accordance with the present disclosure.
Figure 12B:
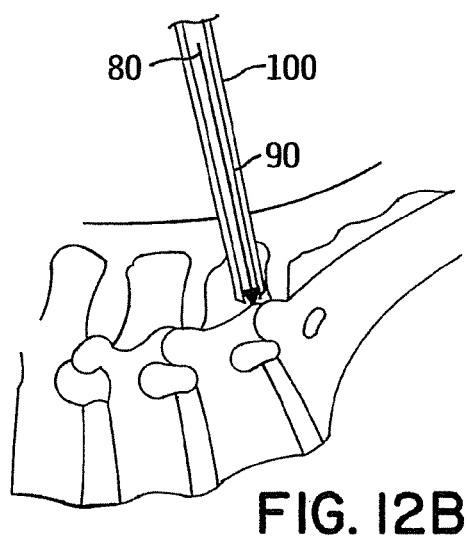
Figure 12C:
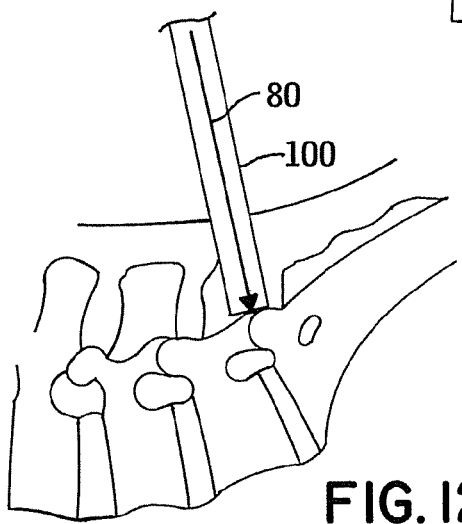

The cannulated dilator 90 or cannulated guide pin (described above) with the conical, tapered distal end 92, the dilator or pin being either straight or curved, is advanced through the soft tissue which is present between the skin access and the point of entry in the facet joint 20, using imaging guidance, either preceding insertion of the guide wire, or else by insertion of the distal end of the dilator over the deployed guide wire, or by concurrent insertion of the dilator and guide wire (e.g., as an "assembly") to create subcutaneous space for the working channel, a mallet or hammer is then used to dock the cannulated dilator into the facet. It will be understood that, for example as needed for other anatomically located joint therapies, this process may be sequentially repeated as needed, i.e., by then inserting a cannulated dilator of larger outer diameter (e.g., from between about 2 mm to about 8 mm in outer diameter) to successively enlarge the access tract. Then, the dilator sheath 100 (e.g., about 3 mm to 10 mm in diameter) is inserted over the guide wire 80 and sheathed over the docked cannulated dilator 90 and into the joint 20 as shown in FIGS. 12A-12C. Upon un-docking and removal of the cannulated dilator 90 from within the sheath 100 and back over the guide wire 80 and out of the patient, the dilator sheath 100 is left in place to serve as a working cannula that provides a protected portal through the soft tissue access tract to the operative site through which subsequent instruments and implant assemblies 90 are delivered through the intervening soft tissue to the target facet joint 20. With ongoing use of fluoroscopic or other imaging guidance to appropriately maintain alignment, next inserted is the cannulated drill 110 (FIG. 7A) that is deployed over the guide wire 80 and through the portal to the surgical site where it is used to bore a cylindrical channel into and across the joint space 20.

In one mode of use, the distal end 114 (FIG. 7A) of the drill 110 is used to finely and precisely penetrate bone on both articulating surfaces of the facet joint 20 to extend the working channel into and across the joint targeted for treatment (e.g., the facet joints), by inserting it (distal end first) into the articular space at the end of the working cannula 100 used as a protected portal, then the drill 110 is rotated by turning the proximal end of the twist drill so that the helical flutes 118 (FIG. 7A) advance into tissue.

The diameter of the channel that is created into the joint 20 is approximately equal to, or slightly less than, the minor diameter of the set of external threads 60 (FIG. 2) on the implant assembly 40 (FIG. 2), i.e., the diameter of the mated halves of the prosthetic anchored articular surfaces to be pre-loaded and delivered via the introducer driver 150 (FIG. 9A). Thus, the bore diameter of the channel is typically from between about 3 mm to about 10 mm. The length of the channel bore is approximately equal to, or slightly less than, the length of the prosthetic implant, about 6 mm to about 25 mm in length.

Following removal of the cannulated drill 110 from the channel, back over the guide wire 80 and out of the patient, the cannulated tap 130 (FIG. 8A) is then inserted over the guide wire 80 and through the working cannula 100 portal to the target site channel. The tap 130 is then rotated to pre-thread the channel. More specifically, the tap 130 is advanced by turning the proximal end so that the flutes and threads at the distal end 134 (FIG. 8A) of the tap progressively cut a thread path into the pilot hole bored into the bone, i.e., to pre-thread a path to facilitate the subsequent insertion of anchored articulating assemblies 40 (FIG. 2) into the joint. It will be understood that in an alternative aspect of the disclosure, an implant assembly that is configured, for example, with component anchoring surfaces that include self-drilling threads rather than self-tapping threads and/or a leading end that comprises a chip breaker, is inserted into a pilot hole bored into the bone that is not tapped to pre-thread the pilot hole.

Once the channel has been tapped, following removal of the cannulated tap 130 from the channel, back over the guide wire 80 and out of the patient, the guide wire 80 is also removed. The working cannula 100 remains as a portal to the target site, into and through which next inserted is a pre-loaded, implant assembly—introducer assembly unit (including a selected implant assembly, a driver, and a tube, with like, "in-kind" thread configuration), for convenience hereinafter termed "implant-introducer unit."

With respect to implant assembly selection, once the clinician has achieved the desired placement, trajectory and depth, a determination of associated, appropriate facet implant assembly length is made based on radiographic measurements, use of intra-operative templates and/or use of depth markers on the guide wire, or a combination of pre-operative imaging measurements and intra-operative trialing. For example, the length of the facet 20 could be pre-measured using fluoroscopic guidance (A-P or oblique view) and then templated to allow for magnification factor.

While in general, the components of an implant assembly will likely be the same in length, it will be understood that in an alternative aspect of the present disclosure, the superior and inferior components in an implant assembly may be selected that vary dimensionally or geometrically, one from the other. It is generally preferred that contact area between superior and inferior prosthetic articulating surfaces be maximized, and that implant component anchoring surfaces generally maximally contact and engage the native articulating bone of the joint.

Figure 13A:
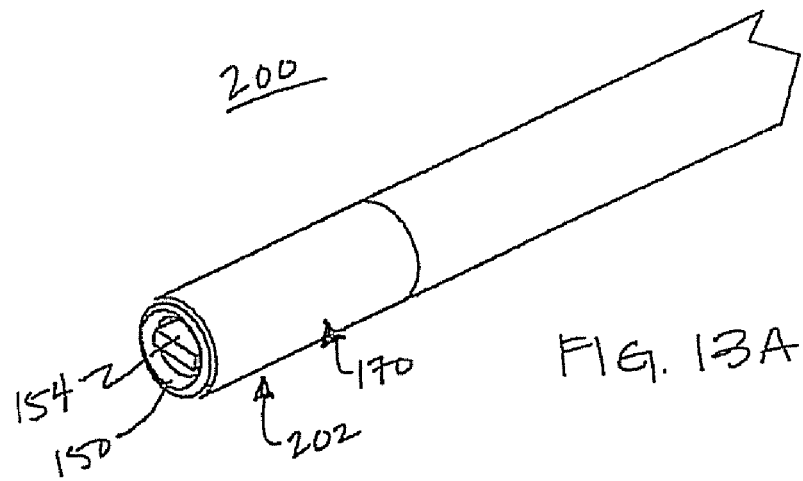
FIG. 13A is an enlarged, perspective view of a driver-tube sub-assembly in accordance with principles of the present disclosure.

In some embodiments, and with reference to FIGS. 9A and 10A, the pre-loaded implant-introducer unit is formed by first inserting the distal end 154 of the driver 150 into the tube 170 and advancing the driver 150 distally until further advancement is precluded when the driver handle 158, that serves as a stop to forward (but not rotational) motion, abuts the proximal end 174 of the tube 170. The resulting driver-tube sub-assembly 200 is shown in FIG. 13A, and reflects that relative to a distal region 202 of the sub-assembly 200, the male flathead projection 154 of the driver 150 (the orientation of which is tracked by indicia on the driver handle) is accessible though the tube 170 for pre-loading of the selected implant components.

Figure 13B:
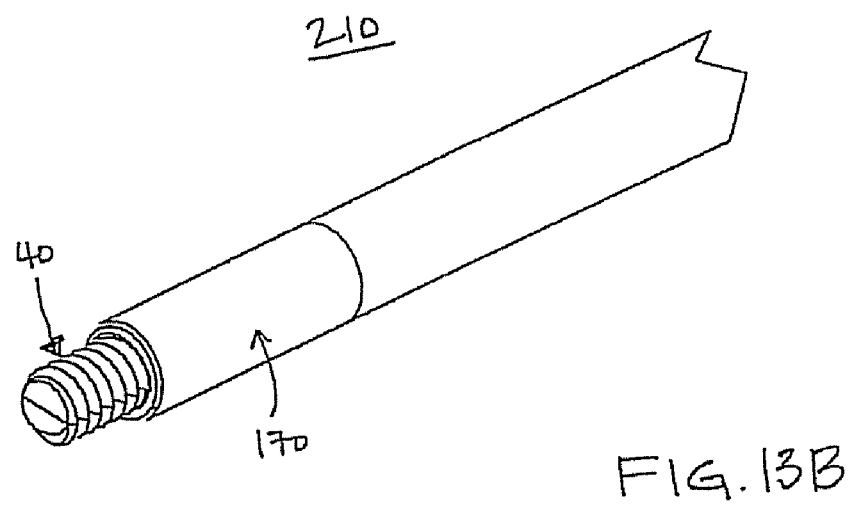
FIG. 13B is an enlarged, perspective view of an implant-introducer unit in accordance with principles of the present disclosure.

With additional reference to FIG. 2, the flat surfaces of the trailing ends 52a, 52b of the implant components 42, 44 each of which are configured as half of the female fixture 70 are then inserted over, to engage and mate with, one of the two opposing flat surfaces of the male flathead projection 154 of the driver 150, thereby forming the implant assembly 40 as extending distally beyond the distal region 202 of the driver-tube sub-assembly 200. The introducer tube 170 is then advanced distally, by rotating the tube 170 (e.g., clockwise for right-handed threads) so that the internal female threads 176 (FIG. 10B) configured in the distal end 172 of the tube 170 engage and advance over the external male threads 162 of the driver 150 and over the external male threads 60 of the implant assembly 40, to advance over and "cover" the implant assembly 40, and resulting in an implant-introducer unit 210 as seen in FIG. 13B. In this manner, the introducer tube 170 secures and holds the threaded implant assembly 40, enabling the implant 40 to be deployed without shifting, and to be atraumatically inserted through soft tissue of the access tract.

Returning to FIGS. 12A-12C and with further reference to FIG. 13B, the deployment of the implant-introducer unit 210 through the working cannula 100 to the target site is achieved by insertion of a distal end 212 of the implant-introducer unit 210 into the working cannula 100 and distally advancing the implant-introducer unit 210 until further forward motion through the working cannula 100 is precluded by the shoulder stop 180 (FIG. 10A) at the proximal end of the introducer tube 170. At this point, the handle 158 (FIG. 9A) at the proximal end of the driver 150 is rotated to distally advance the external threads 162 (FIG. 9A) of the driver 150 through the internal threads 176 of the tube 170 which advances the external threads 60 of the implant assembly 40, engaged to the driver 150, distally through the internal threads 176 of the tube 170. In this manner, the implant assembly 40 is thereby driven to extend beyond the distal end of the tube 170 until further advancement of the implant assembly 40 into the joint 20 by the driver 150 is precluded by the driver distal stop, i.e., the handle 158 at the proximal end of the driver 150 abuts the proximal end of the tube 170. In this manner, and by appropriately orienting the indicia provided on the introducer sub-assembly 200, the clinician is also concurrently deploying and aligning the inferior implant component 44 on the inferior articular facet and the superior implant component 42 on the superior articular facet such that the anchoring surfaces 54 of the inferior implant component 44 interact and engage with the native bone of the articulating surface of the inferior facet; and the anchoring surface 54 of the superior implant component 42 interacts and engages with the native bone of the articulating surface of the superior facet as shown in FIG. 3C.

A second prosthetic facet implant assembly 40 may then introduced through a new skin incision and aligned trajectory by repeating the deployment steps as just described on the other side of the spinous process (bilateral/contralateral). That is, under fluoroscopic guidance, the guide wire 80 is introduced into the second joint, the dilator 90 and dilator sheath 100 are inserted over the guide wire 80 and passed into the joint space 20, the dilator 90 is removed and the cannulated drill 110 is inserted over the guide wire 80 and through the protected working portal to drill the pilot hole to a channel depth that ideally is equal to or closely approximates the length of the implant assembly 40 to be deployed and a channel diameter that is slightly less than the implant assembly 40; the depth of the hole can then measured; the drill 110 is removed and the tap 130 is used to pre-thread the entire length of the hole; the guide pin 80 is removed and the selected and appropriately sized implant assembly 40, that is pre-loaded onto and within an introducer driver-introducer tube sub-assembly 200, is deployed through the working channel into the pilot hole, where it is inserted and anchored into the joint 20 via rotation and alignment of the introducer driver 150 to advance the implant assembly 40 its final aligned position within the articular space 20, to augment the native joint articulation surfaces.

Once the implant assembly components have been deployed and instrumentation removed from the posterior access track, site closure is performed by the clinician.

Kits

Kits may be provided that include all of the components necessary for deploying the implant assemblies and therapies described above. The kits may also include some or all of the necessary guide wires, dilators, cannula, drills, taps, and implant insertion tool assemblies as set forth above. The kits may also include components and instrument sizes and implants in a variety of sizes and configurations to address the variations in facet joints from one portion of a spine to another, from one patient to another, and to address irregularities that may be present from degeneration of the facet joint. For example, it is anticipated that implant assemblies can be provided in a range of predetermined sizes (e.g., small, medium, large) and or configurations (e.g., cervical, thoracic, lumbar) to allow a clinician to choose an appropriate size and shape for the patient, to conform anatomically or to achieve a desired level of distraction. It is also contemplated that kits be provided, for example, that comprise implant assemblies that have been customized for a particular patient.

Terminology

In the context of the present disclosure, as used herein the term "assembly" refers to implants, instruments and instruments systems which are configured to comprise multiple components, which may or may not be contiguous. It is further understood that individual components may themselves be configured as sub-assemblies, e.g., comprising a plurality of component materials, and that the formation of the components may involve intermediate processes or appliances.

It will also be understood that upon formation of assemblies from multiple components and deployment, individual components may or may not remain as discernibly distinct.

It will also be understood that the components, in whole or in part, may be designed to be bioabsorbable or non-degradable as clinically indicated.

In accordance with one aspect of the examples described herein, there are provided certain materials which can enhance visualization of implant assembly components and instrumentation for their deployment via radio-imaging (e.g., fluoroscopy). It will be understood that such enhancing materials (e.g., Ta; barium sulfate powders; etc.) may be incorporated into the formation of certain metal or polymeric materials comprised in the device assemblies and/or tools sets used to deploy the devices of the present disclosure.

In the context of the present disclosure, as used herein the term distraction refers procedurally to an elevation in height in the facet joint capsule resulting from (optional) introduction of prosthetic implant assemblies, i.e., during facet joint device deployment. The physical anchoring and dimensionality of the inserted prosthetic implants comprised within the device assemblies of the present disclosure are key to preserving that height space, to decompress the joint and alleviate pain caused by nerve impingement.

In the context of the present disclosure, "dynamic" refers to non-static devices with an inherent ability to allow mobility by enabling or facilitating force or load bearing that assist or substitute for physiological structures that are otherwise compromised, weakened or absent. The spinal motion preservation assemblies of the present disclosure provide dynamic stabilization across a progression-of-treatment interventions for treating symptomatic joint pain.

As used herein, the term "biocompatible" refers to an absence of chronic inflammation response or cytotoxicity when or if physiological tissues are in contact with, or exposed to (e.g., wear debris) the materials and devices of the present disclosure. In addition to biocompatibility, in another aspect of the present disclosure it is preferred that the materials comprising the instrument systems (e.g., drills; taps; etc.) are sterilizable; visible and/or imageable, e.g., fluoroscopically; or via CT (computed tomography), or if via MRI (magnetic resonance imaging), with this last-named imaging technique mandating that materials be substantially free of Fe (iron). Moreover, in consideration of contrast, detail, and spatial sensitivity, it is preferred that contrast media (e.g., iodine) or other materials (e.g., Ta; Ti) be employed in configuring instrumentation when and where needed and appropriate, to supplement or modify radiolucency or radiopaqueness.

In one aspect of the present disclosure, certain components of the device assemblies and systems of the present disclosure are configured to comprise biocompatible materials and are able to withstand, without wear, multiple cycles/procedures without failing. In the context of this disclosure, it will be understood that the term "material" may sometimes be a combination of the composition and treatments to produce desired properties and or performance.

It will be understood that the surgical access can be conducted by methods other than the approaches described, including without limitation open surgical procedures from any access orientation, and that each of the therapies to the spine can be conducted on more than one motion segments (e.g., cervical as well as lumbar) traversed by at least one working channel, with deployment of appropriate implants and with post-procedural surgical closure. Only for convenience, the exemplary access by the method, instrumentation, and treatment of facet joints in only a single motion segment are described in detail herein, in accordance with the instrument systems and prosthetic devices of the present disclosure.

It will be further understood that the length and dimensions of instruments and implant components (e.g., bone screws) described herein will depend in part on the nature of the treatment procedure (for example, treatment level, e.g., cervical, thoracic, lumbar) and the physical characteristics of the patient, as well as the construction materials and intended functionality, as will be apparent to those of skill in the art.

The effort to provide one or more tangible examples in order to promote the understanding of the present disclosure should not be misinterpreted as a limitation on the scope of the disclosure as the scope of the disclosure is set forth in the claims that may be constructed from and commensurate with the disclosure as disclosed and described herein.

For example, one of skill in the art will appreciate that indicia/landmarks for establishing and maintaining driver-implant-joint orientation and alignment during prosthesis insertion could be implemented by various other alternative methods or tools not shown.

One of skill in the art will recognize that in some cases that the order of the steps set forth above may be changed without departing from the teachings of this disclosure. Some implementations, particularly those involving placement of guide wire/guide pin tips into bone, may benefit from having a threaded portion of the guide pin to help maintain the precise position of the guide pin during the use of the instrumentation systems disclosed herein, or alternatively the use of guide pin tips of similar geometries to those of, e.g., the instrument system drills.

One of skill in the art will recognize that alternative implementations set forth above are not universally mutually exclusive and that in some cases additional implementations can be created that implement two or more of the variations described above. In a like manner, one of skill in the art will recognize that certain aspects of the present disclosure can be implemented without implementing all of the teachings illustrated in any of the various disclosed implementations. Such partial implementations of the teachings of the present disclosure fall within the claimed subject matter unless the claims are explicit in calling for the presence of additional elements from other teachings.

In order to promote clarity in the description, common terminology for components is used. The use of a specific term for a component suitable for carrying out some purpose within the disclosed disclosure should be construed as including all technical equivalents which operate to achieve the same purpose, whether or not the internal operation of the named component and the alternative component use the same principles. The use of such specificity to provide clarity should not be misconstrued as limiting the scope of the disclosure to the named component unless the limitation is made explicit in the description or the claims that follow.

In order to make it easier for a reader to find certain sections of this document that are of particular interest to the reader, a series of headings have been used. These headings are solely for the purpose of helping readers navigate the document and do not serve to limit the relevance of any particular section to exclusively the topic listed in the heading.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "anchored" on, "affixed" on, "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present disclosure. The sequence of operations (or steps) is not limited to the order presented in the claims or figures unless specifically indicated otherwise.

The terms "implant", "implant assembly," "prosthesis" and "prosthetic device" are used interchangeably to describe a medical product that is configured to reside in a target face joint of a mammalian subject (for veterinary or medical (human) applications). A facet implant or prosthesis can be applied to one surface (one side) of the facet joint (the bone is resurfaced by the implant) or to both surfaces of the joint, and/or may reside therebetween as a spacer or liner that, in response to loads introduced by the cooperating bones at the facet joint, still allows motion therebetween.

Those skilled in the art will recognize that the methods and apparatus of the present disclosure have many applications and that the present disclosure is not limited to the specific examples given to promote understanding of the present disclosure. Moreover, the scope of the present disclosure covers the range of variations, modifications, and substitutes for the system components described herein, as would be known to those of skill in the art.

What is claimed is:

1. A spinal facet implant system for treating a facet joint of a patient, the facet joint including opposing, superior and inferior faces, the spinal facet implant system comprising:
    an elongated superior facet component defining a cylindrical-like anchoring surface, configured to engage bone at a superior face of the facet joint, and an opposing articulating surface; and
    an elongated inferior facet component defining a cylindrical-like anchoring surface, configured to engage bone at an inferior face of the facet joint, and an opposing articulating surface;
    wherein each of the articulating surfaces is planar across a width of the component;
    wherein the width extends between opposing sides of the component;
    wherein each of the anchoring surfaces comprises a thread;
    wherein the superior and inferior components combine to define an exteriorly threaded cylindrical rod upon final assembly;
    wherein the spinal facet implant system is configured for percutaneous insertion into the facet joint, with the articulating surfaces abutting one another in a sliding interface; and
    wherein the spinal facet implant system is characterized by the absence of a mechanical connection between the superior and inferior components upon implantation into a facet joint.

2. The spinal facet implant system of claim 1, wherein one of the articulating surfaces is convex and another of the articulating surfaces is concave.

3. The spinal facet implant system of claim 1, wherein the anchoring surfaces each include at least one projection configured to self-embed into bone.

4. The spinal facet implant system of claim 1, wherein the spinal facet implant system has a length greater than a height or width, and the length is not greater than 30 mm.

5. The spinal facet implant system of claim 4, wherein each of the anchoring surfaces includes at least one fixation member projecting from a contact face, and further wherein the height is defined as a linear dimension between the opposing contact faces, and even further wherein the height is not greater than 4 mm.

6. The spinal facet implant system of claim 5, wherein the width is not greater than 5 mm.

7. The spinal facet implant system of claim 1, wherein the superior and inferior components are identical.

8. A kit for treating a facet joint of a patient, the facet joint including opposing, superior and inferior faces, the kit comprising:
    a spinal facet implant system including:
        an elongated superior facet component defining a cylindrical-like anchoring surface, configured to engage bone at a superior face of the facet joint, and an opposing articulating surface; and
        an elongated inferior facet component defining a cylindrical-like anchoring surface, configured to engage bone at an inferior face of the facet joint, and an opposing articulating surface;
        wherein each of the articulating surfaces is planar across a width of the component; wherein the width extends between opposing sides of the component;
        wherein each of the anchoring surfaces comprises a thread;
        wherein the superior and inferior components combine to define an exteriorly threaded cylindrical rod upon final assembly;
        wherein the spinal facet implant system is configured for percutaneous insertion into the facet joint, with the articulating surfaces abutting one another in a sliding interface; and
        wherein the spinal facet implant system is characterized by the absence of a mechanical connection between the superior and inferior components upon implantation into a facet joint; and
    a dilator configured to percutaneously dilate the facet joint for percutaneous insertion of the implant spinal facet implant system therein.

9. The kit of claim 8, wherein the spinal facet implant has a length greater than a height or width, and the length is not greater than 30 mm.

10. The kit of claim 9, wherein each of the anchoring surfaces includes at least one fixation member projecting from a contact face, and further wherein the height is defined as a linear dimension between the opposing contact faces, and even further wherein the height is not greater than 4 mm.

11. The kit of claim 10, wherein the width is not greater than 5 mm.

12. The kit of claim 8, wherein the superior and inferior components are identical.

13. The kit of claim 8, further comprising:
    a cannula defining an inner diameter sized to slidably receive the dilator and configured to percutaneously access a facet joint.

14. The kit of claim 8, further comprising:
    a guide wire configured to percutaneously access a facet joint;
    wherein the dilator forms a lumen sized to slidably receive the guide wire.

* * * * *